(12) United States Patent
Gududuru

(10) Patent No.: US 8,686,177 B2
(45) Date of Patent: Apr. 1, 2014

(54) LPA RECEPTOR AGONISTS AND ANTAGONISTS

(75) Inventor: Veeresh Gududuru, Memphis, TN (US)

(73) Assignee: RxBio, Inc., JOhnson City, TN (US)

( * ) Notice: Subject to any disclaimer, the term of this patent is extended or adjusted under 35 U.S.C. 154(b) by 0 days.

(21) Appl. No.: 12/921,140

(22) PCT Filed: Mar. 3, 2009

(86) PCT No.: PCT/US2009/035931
§ 371 (c)(1),
(2), (4) Date: Apr. 4, 2011

(87) PCT Pub. No.: WO2010/051053
PCT Pub. Date: May 6, 2010

(65) Prior Publication Data
US 2012/0010424 A1    Jan. 12, 2012

Related U.S. Application Data

(60) Provisional application No. 61/033,386, filed on Mar. 3, 2008.

(51) Int. Cl.
*C07F 9/177*    (2006.01)
(52) U.S. Cl.
USPC .......................................................... 558/209

(58) Field of Classification Search
USPC .......................................................... 558/208
See application file for complete search history.

(56) References Cited

U.S. PATENT DOCUMENTS

| 7,217,704 B2 * | 5/2007 | Miller et al. | 514/144 |
| 2006/0009507 A1 * | 1/2006 | Miller et al. | 514/408 |

FOREIGN PATENT DOCUMENTS

| WO | WO2007/011905 | * | 1/2007 |

* cited by examiner

*Primary Examiner* — Rebecca Anderson
*Assistant Examiner* — Karen Cheng
(74) *Attorney, Agent, or Firm* — Lihua Zheng; Mary Consalvi; Proskauer Rose LLP

(57) ABSTRACT

Disclosed are compounds according to formula (I) as well as pharmaceutical compositions which include those compounds. Also disclosed are methods of using such compounds, which have activity as agonists or as antagonists of LPA receptors; such methods including treating cancer, producing radioprotection and/or radiomitigation, enhancing cell proliferation, treating a wound, treating apoptosis or preserving or restoring function in a cell, tissue, or organ, culturing cells, preserving organ or tissue function, and treating a dermato logical condition.

2 Claims, 5 Drawing Sheets

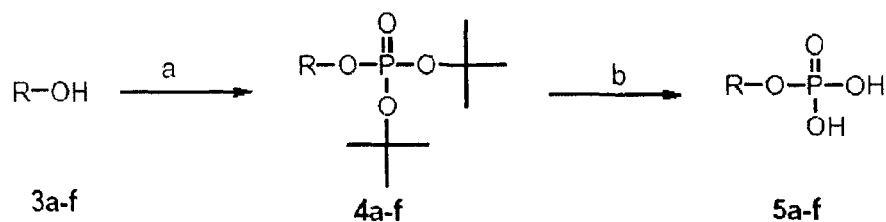
Scheme 1
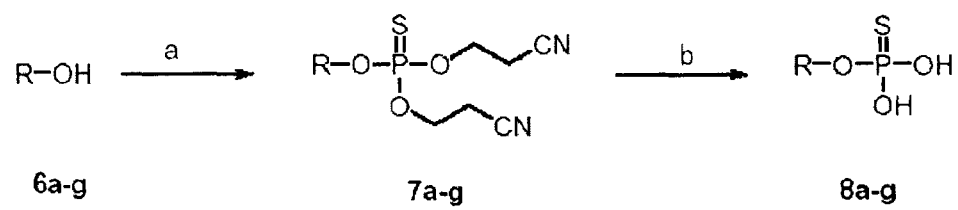
Scheme 2
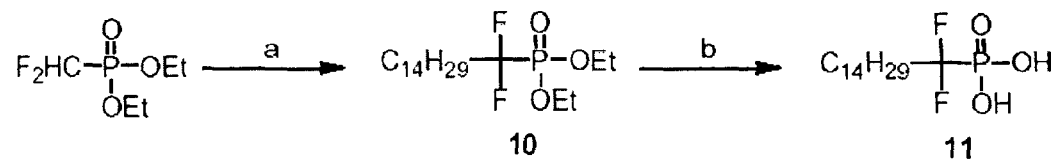
Scheme 3
Fig. 1

Fig. 2A-C

LPA RECEPTOR AGONISTS AND ANTAGONISTS

CROSS-REFERENCE TO RELATED APPLICATIONS

This application claims the benefit of priority of earlier-filed U.S. provisional patent application No. 61/033,386, filed Mar. 3, 2008.

FIELD OF THE INVENTION

This invention relates to compositions which have activity as agonists or antagonists of lysophosphatidic acid (LPA) receptors and methods for their use.

BACKGROUND OF THE INVENTION

Lysophosphatidic acid (LPA) modulates metabolic responses as diverse as neuropathic pain, healing responses of human periodontal ligament fibroblasts, wound healing, radiation injury, immune-cell differentiation, cell proliferation, cell survival and cell migration. Lysophosphatidic acid receptors have been identified, and some of these effects appear to be correlated with the specific receptor to which LPA binds. For example, among the uses that the inventors have previously identified for molecules that they have identified as LPA agonists or antagonists is the benefit provided by oleoyl thiophosphate as a radioprotectant and radiomitigator. Modulating LPA-related metabolic pathways using receptor-specific agonists and antagonists therefore provides an exciting opportunity to develop therapeutic agents for a number of disease states.

SUMMARY OF THE INVENTION

The present invention relates to compounds according to formula (I)

$$CQ^1-CH(X^3)-CQ^2$$
with $X^1$ and $X^2$ (I)

wherein, at least one of $X^1$, $X^2$, and $X^3$ is $(HO)_2PS-Z^1-$, $(HO)(BH_3)PO-Z^1-$, or $(HO)_2PO-Z^2-P(OH)S-Z^1-$, $X^1$ and $X^2$ are linked together as $-O-PS(OH)-O-$, or $X^1$ and $X^3$ are linked together as $-O-PS(OH)-NH-$;

at least one of $X^1$, $X^2$, and $X^3$ is $R^1-Y^1$-A- with each being the same or different when two of $X^1$, $X^2$, and $X^3$ are $R^1-Y^1$-A-, or $X^2$ and $X^3$ are linked together as $-N(H)-C(O)-N(R^1)-$;

optionally, one of $X^1$, $X^2$, and $X^3$ is H;

A is either a direct link, $(CH_2)_k$ with k being an integer from 0 to 30, or O;

$Y^1$ is $-(CH_2)_l-$ with l being an integer from 1 to 30, $-O-$, $-S-$, $$-\overset{O}{\underset{\|}{C}}-$$

or $-NR^2-$;

$Z^1$, is $-(CH_2)_m-$, $-CF_2-$, $-CF_2(CH_2)_m-$, or $-O(CH_2)_m-$ with m being an integer from 1 to 50, $-C(R^3)H-$, $-NH-$, $-O-$, or $-S-$;

$Z^2$ is $-(CH_2)_n-$ or $-O(CH_2)_n-$ with n being an integer from 1 to 50 or $-O-$;

$Q^1$ and $Q^2$ are independently $H_2$, $=NR^4$, $=O$, or a combination of H and $-NR^5R^6$;

$R^1$, for each of $X^1$, $X^2$, or $X^3$, is independently hydrogen, a straight or branched-chain C1 to C30 alkyl optionally substituted with cycloalkyl, a straight or branched-chain C2 to C30 alkenyl optionally substituted with cycloalkyl, an aromatic or heteroaromatic ring with or without mono-, di-, or tri-substitutions of the ring, an acyl including a C1 to C30 alkyl or an aromatic or heteroaromatic ring, an arylalkyl including straight or branched-chain C1 to C30 alkyl, an aryloxyalkyl including straight or branched-chain C1 to C30 alkyl, $$-CH=NH_2,$$ imidazoline with $R^7$ and $R^8$, imidazole with $R^7$ and $R^8$,
$$-C(=NR^8)-NH-R^7, \quad -C(=O)-NH-R^7, \quad -C(=S)-NH-R^7,$$
$$-C(=O)-O-R^7;$$

and $R^2$, $R^3$, $R^4$, $R^5$, $R^6$, $R^7$, and $R^8$ are independently hydrogen, a straight or branched-chain C1 to C30 alkyl optionally substituted with cycloalkyl, a straight or branched-chain C2 to C30 alkenyl optionally substituted with cycloalkyl, an aromatic or heteroaromatic ring with or without mono-, di-, or tri-substitutions of the ring, an acyl including a C1 to C30 alkyl or aromatic or heteroaromatic ring, an arylalkyl including straight or branched-chain C1 to C30 alky, or an aryloxyalkyl including straight or branched-chain C1 to C30 alkyl.

Also disclosed are pharmaceutical compositions which include a pharmaceutically-acceptable carrier and a compound of the present invention.

A further aspect of the present invention relates to a method of inhibiting LPA activity on an LPA receptor which includes providing a compound of the present invention which has activity as an LPA receptor antagonist and contacting an LPA receptor with the compound under conditions effective to inhibit LPA-induced activity of the LPA receptor.

Another aspect of the present invention relates to a method of modulating LPA receptor activity which includes providing a compound of the present invention which has activity as either an LPA receptor agonist or an LPA receptor antagonist and contacting an LPA receptor with the compound under conditions effective to modulate the activity of the LPA receptor.

Still another aspect of the present invention relates to a method of treating cancer which includes providing a compound of the present invention and administering an effective amount of the compound to a patient in a manner effective to treat cancer.

Yet another aspect of the present invention relates to a method of enhancing cell proliferation which includes providing a compound the present invention which has activity as an agonist of an LPA receptor and contacting the LPA receptor on a cell with the compound in a manner effective to enhance LPA receptor-induced proliferation of the cell.

A further aspect of the present invention relates to a method of treating a wound which includes providing a compound of the present invention which has activity as an agonist of an LPA receptor and delivering an effective amount of the compound to a wound site, where the compound binds to LPA receptors on cells that promote healing of the wound, thereby stimulating LPA receptor agonist-induced cell proliferation to promote wound healing. Also provided is a method for preventing or mitigating radiation injury to cells and tissues, compounds of the invention having been shown to be effective radioprotectants and radiomitigators.

A still further aspect of the present invention relates to a method of making the compounds of the present invention. One approach for making the compounds of the present invention includes:

reacting $(Y^2O)_2PO-Z^{11}-Z^{13}$ or $(Y^2O)_2PO-Z^{12}-P(OH)-O-Z^{11}-Z^{13}$, where $Z^{11}$ is $-(CH_2)_m-$, $CF_2-$, $-CF_2(CH_2)_m-$, or $-O(CH_2)_m-$ with m being an integer from 1 to 50, $-C(R^3)H-$, $-NH-$, or $-S-$;

$Z^{12}$ is $-(CH_2)_n-$ or $-(CH_2)_n-$ with n being an integer from 1 to 50 or $-O-$, $Z^{13}$ is H or a first leaving group or $-Z^{11}-Z^{13}$ together form the first leaving group; and $Y^2$ is H or a protecting group, with an intermediate compound according to formula (IX) in the presence of sulfur

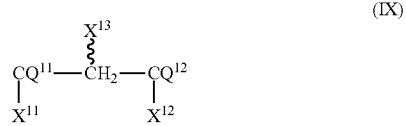

where, at least one of $X^{11}$, $X^{12}$, and $X^{13}$ is $R^{11}-Y^{11}-A-$ with each being the same or different when two of $X^{11}$, $X^{12}$, and $X^{13}$ are $R^{11}-Y^{11}-A-$, or $X^{12}$ and $X^{13}$ are linked together as $-N(H)-C(O)-N(R^{11})-$;

at least one of $X^{11}$, $X^{12}$, and $X^{13}$ is OH, $NH_2$, SH, or a second leaving group;

optionally, one of $X^{11}$, $X^{12}$, and $X^{13}$ is H;

A is either a direct link, $(CH_2)_k$ with k being an integer from 0 to 30, or O;

$Y^{11}$ is $-(CH_2)_l-$ with l being an integer from 1 to 30, $-O-$,

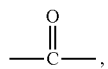

$-S-$, or $-NR^{12}-$;

$Q^1$ and $Q^2$ are independently $H_2$, $=NR^{13}$, $=O$, a combination of H and $-NR^{14}R^{15}$;

$R^{11}$, for each of $X^{11}$, $X^{12}$, or $X^{13}$, is independently hydrogen, a straight or branched-chain C1 to C30 alkyl, a straight or branched-chain C2 to C30 alkenyl, an aromatic or heteroaromatic ring with or without

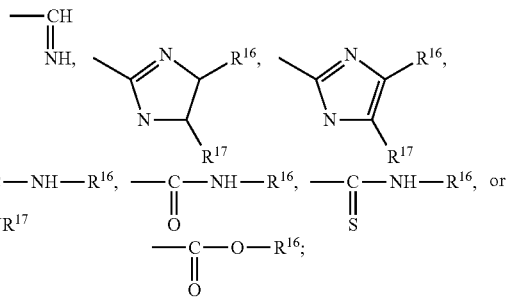

and mono-, di-, or tri-substitutions of the ring, an acyl including a C1 to C30 alkyl or an aromatic or heteroaromatic ring, an arylalkyl including straight or branched-chain C1 to C30 alkyl, an aryloxyalkyl including straight or branched-chain C1 to C30 alkyl, $R^{12}$, $R^{13}$, $R^{14}$, $R^{15}$, $R^{16}$, and $R^{17}$ are independently hydrogen, a straight or branched-chain C1 to C30 alkyl, a straight or branched-chain C2 to C30 alkenyl, an aromatic or heteroaromatic ring with or without mono-, di-, or tri-substitutions of the ring, an acyl including a C1 to C30 alkyl or aromatic or heteroaromatic ring, an arylalkyl including straight or branched-chain C1 to C30 alkyl, or an aryloxyalkyl including straight or branched-chain C1 to C30 alkyl; followed by a de-protection step, if necessary, with both said reacting and the deprotection step being performed under conditions effective to afford a compound according to formula (I) where one or two of $X^1$, $X^2$, and $X^3$ is $(HO)_2PS-Z^1-$ or $(HO)_2PS-Z^2-P(OH)S-Z^1-$.

Yet another aspect of the present invention relates to a method of treating apoptosis or preserving or restoring function in a cell, tissue, or organ which includes: providing a compound of the present invention which has activity as an agonist of an LPA receptor; and contacting a cell, tissue, or organ with an amount of the compound which is effective to treat apoptosis or preserve or restore function in the cell, tissue, or organ.

A further aspect of the present invention relates to a method of culturing cells which includes: culturing cells in a culture medium which includes a compound of the present invention which has activity as an agonist of an LPA receptor and is present in an amount which is effective to prevent apoptosis or preserve the cells in culture.

Another aspect of the present invention relates to a method of preserving an organ or tissue which includes: providing a compound of the present invention which has activity as an agonist of an LPA receptor; and treating an organ or tissue with a solution comprising the compound in an amount which is effective to preserve the organ or tissue function.

A related aspect of the present invention relates to an alternative method of preserving an organ or tissue which includes: providing a compound of the present invention which has activity as an agonist of an LPA receptor; and administering to a recipient of a transplanted organ or tissue an amount of the compound which is effective to preserve the organ or tissue function A still further aspect of the present invention relates to a method of treating a dermatological condition which includes: providing a compound of the present invention which has activity as an LPA receptor agonist; and topically administering a composition comprising the compound to a patient, the compound being present in an amount which is effective to treat the dermatological condition The compounds of the present invention which have been identified herein as being either agonists or antagonists of one or more LPA receptors find uses to inhibit or enhance, respectively, biochemical pathways mediated by LPA receptor signaling. By modulating LPA receptor signaling, the antagonists and agonists find specific and substantial uses as described herein.

BRIEF DESCRIPTION OF THE DRAWINGS

FIG. 1 illustrates three reaction schemes used to prepare fatty acid phosphates (Scheme 1), fatty acid thiophosphonates (Scheme 2), and difluorophosphonates (Scheme 3).

DETAILED DESCRIPTION OF THE INVENTION

Figure 2:
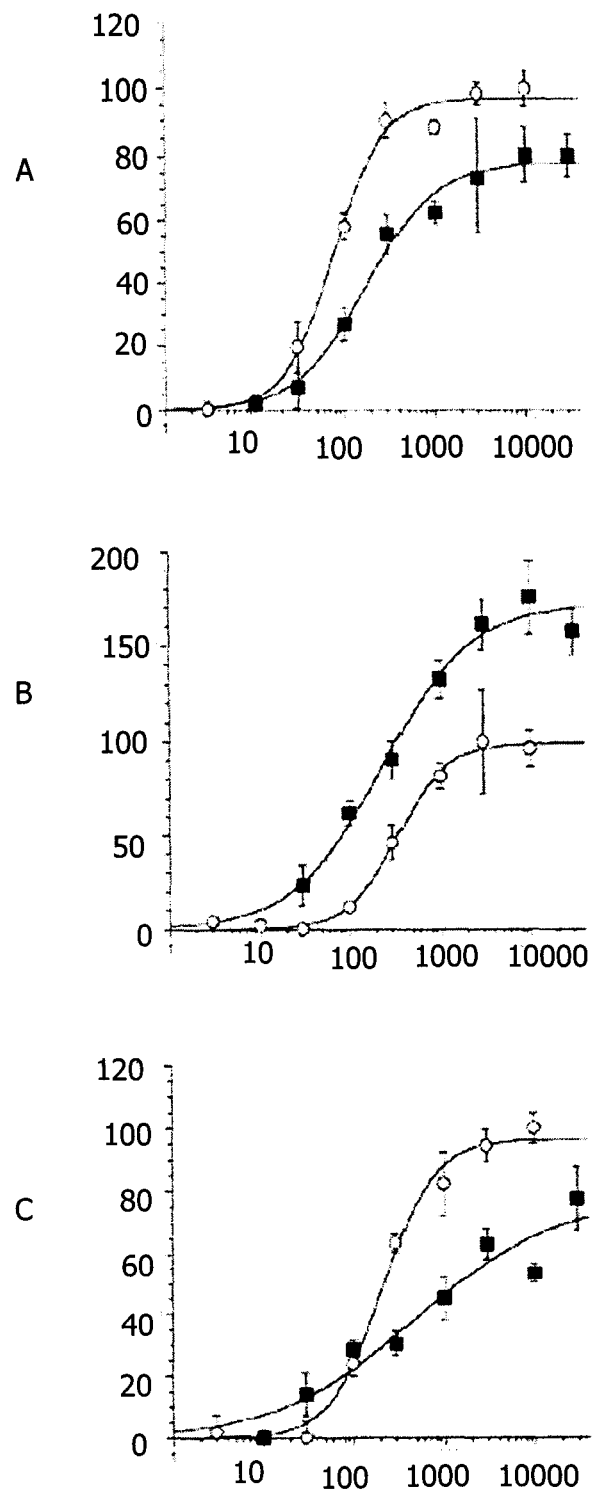
FIGS. 2A-C are graphs illustrating that oleoyl-thiophosphate (8g) is an agonist at $LPA_1$, $LPA_2$ and $LPA_3$ receptors expressed in RH7777 cells. Intracellular $Ca^{2+}$ transients were measured in response to the application of increasing concentrations of 8g and compared to transients elicited by the corresponding amount of LPA 18:1. Data points represent the average of four measurements. Dose-response relationships are shown for LPA 18:1 and 8g in RH7777 cells expressing $LPA_1$ (FIG. 2A), $LPA_2$ (FIG. 2B), and $LPA_3$ (FIG. 2C). Y-axis: calcium mobilization, expressed as percent of maximal LPA response±S.D. X-axis: concentration (nM). Open circles indicate results for LPA 18:1 and squares indicate results for oleoyl thiophosphate (OTP, compound 8g).

One aspect of the present invention relates to a compound according to formula (I)

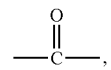

(I)

wherein, at least one of $X^1$, $X^2$, and $X^3$ is $(HO)_2PS—Z^1—$, $(HO)(BH_3)PO—Z^1—$, or $(HO)_2PS—Z^2—P(OH)S—Z^1—$, $X^1$ and $X^2$ are linked together as $—O—PS(OH)—O—$, or $X^1$ and $X^3$ are linked together as $—O—PS(OH)—NH—$;

at least one of $X^1$, $X^2$, and $X^3$ is $R^1—Y^1$-A- with each being the same or different when two of $X^1$, $X^2$, and $X^3$ are $R^1—Y^1$-A-, or $X^2$ and $X^3$ are linked together as $—N(H)—C(O)—N(R^1)—$;

optionally, one of $X^1$, $X^2$, and $X^3$ is H;

A is either a direct link, $(CH_2)_k$ with k being an integer from 0 to 30, or $—O—$;

$Y^1$ is $—(CH_2)_l—$ with l being an integer from 1 to 30, $—O—$,

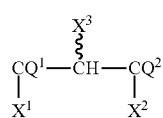

$—S—$, or $—NR^2—$;

$Z^1$ is $—(CH_2)_m—$, $—CF_2—$, $—CF_2(CH_2)_m—$, or $—O(CH_2)_m—$ with m being an integer from 1 to 50, $—C(R^3)H—$, $—NH—$, $—O—$, or $—S—$;

$Z^2$ is $—(CH_2)_n—$ or $—O(CH_2)_n—$ with n being an integer from 1 to 50 or $—O—$;

$Q^1$ and $Q^2$ are independently $H_2$, $=NR^4$, $=O$, a combination of H and $—NR^5R^6$;

$R^1$, for each of $X^1$, $X^2$, or $X^3$, is independently hydrogen, a straight or branched-chain C1 to C30 alkyl optionally substituted with cycloalkyl, a straight or branched-chain C2 to C30 alkenyl optionally substituted with cycloalkyl, an aromatic or heteroaromatic ring with or without mono-, di-, or tri-substitutions of the ring, an acyl including a C1 to C30 alkyl or an aromatic or heteroaromatic ring, an arylalkyl including straight or branched-chain C1 to C30 alkyl, an aryloxyalkyl including straight or branched-chain C1 to C30 alkyl,

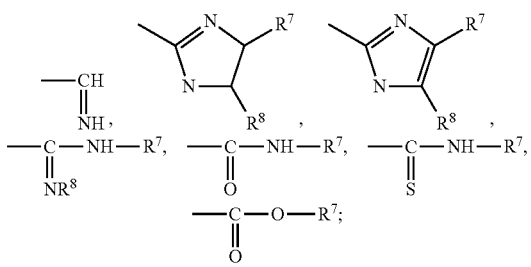

and $R^2$, $R^3$, $R^4$, $R^5$, $R^6$, $R^7$, and $R^8$ are independently hydrogen, a straight or branched-chain C1 to C30 alkyl optionally substituted with cycloalkyl, a straight or branched-chain C2 to C30 alkenyl optionally substituted with cycloalkyl, an aromatic or heteroaromatic ring with or without mono-, di-, or tri-substitutions of the ring, an acyl including a C1 to C30 alkyl or aromatic or heteroaromatic ring, an arylalkyl including straight or branched-chain C1 to C30 alkyl, or an aryloxyalkyl including straight or branched-chain C1 to C30 alkyl.

For each of the above-identified R groups (e.g., $R^1$-$R^8$), straight chain alkyls have the formula $—(CH_2)_xCH_3$ where x is from 0 to 29; branched chain alkyls have the formula as defined above for straight chain alkyl, except that one or more $CH_2$ groups are replaced by CHW groups where W is an alkyl side chain; straight chain alkenyls have the formula $—(CH_2)_{Xa}CH=CH(CH_2)_{Xb}CH_3$ where Xa and Xb each are from 0 to 27 and (Xa+Xb) is not more than 27; and branched chain alkenyls have the formula as defined above for straight chain alkenyl, except that one or more $CH_2$ groups are replaced by CHW groups or a CH group is replaced by a CW group, where W is an alkyl side chain. Preferred hydrocarbon groups are preferably between about 8 to about 18 carbon atoms in length, more preferably between about 10 to about 16 carbon atoms in length, and may contain one or more double bonds. Alkyls and alkenyls which optionally include one or more cycloalkyl substitutions are intended to encompass alkyl and/or alkenyl straight or branched chains which include one or more cyclopropyl rings as part of the chain (i.e., cycloalkyls such as cyclopropyl formed in part by adjacent carbons within the chain) as shown in the structures of RxBVG-I-93, RxBVG-II-93, RxBVG-II-22, RxBVG-II-23, RxBVG-II-34, RxBVG-II-35, RxBVG-II-36, and RxBVG-II-37 in Table 4.

Aromatic or heteroaromatic rings include, without limitation, phenyls, indenes, pyrroles, imidazoles, oxazoles, pyrrazoles, pyridines, pyrimidines, pyrrolidines, piperidines, thiophenes, furans, napthals, bi-phenyls, and indoles. The aromatic or heteroaromatic rings can include mono-, di-, or tri-substitutions of the ring located at the ortho, meta, or para positions on the rings relative to where the ring binds to the $Y^1$ group of the $R^1$—$Y^1$-A- chain. Substitutions on the rings can include, without limitation, alkyl, alkoxy, amine (including secondary or tertiary amines), alkylamine, amide, alkylamide, acids, alcohols.

Acyl groups can include either alkyl, alkenyl, or aromatic or heteroaromatic rings as described above.

Arylalkyl and aryloxyalkyl groups can include, without limitation, straight or branched-chain C1 to C30 alkyl groups as described above, with the alkyl group binding to the $Y^1$ group of the $R^1$—$Y^1$-A- chain.

Exemplary compounds according to formula (I) are the subclass compounds according to formulae (II)-(VII) below.

In the structures of formulae (II)A and (II)B, $Q^1$ and $Q^2$ are both $H_2$; one of $X^1$, $X^2$, and $X^3$ is $(HO)_2PS$—$Z^2$—$P(OH)S$—$Z^1$—, with $Z^1$ and $Z^2$ being O; and two of $X^1$, $X^2$, and $X^3$ are $R^1$—$Y^1$-A-, with A being a direct link and $Y^1$ being O for each. Each $R^1$ is defined independently as above for formula (I).

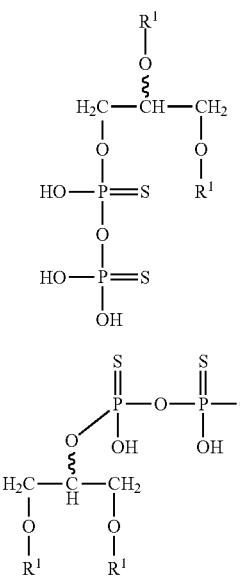

(II)A (II)B

In the structures of formula (III), $Q^1$ is $H_2$; $Q^2$ is —O—: $X^1$ is $(HO)_2PO$—$Z^1$—, with $Z^1$ being O; and $X^2$ and $X^3$ are $R^1$—$Y^1$-A-, with A being a direct link and $Y^1$ being —NH— for each. Each $R^1$ is defined independently as above for formula (I). Preferred species of within the scope of formula III are where $X^3$ is —$NH_2$ and $X^2$ is —$NHR^1$ with $R^1$ being a C10 to C18 alkyl, more preferably either a C14 alkyl or a C18 alkyl; or where $X^3$ is —$NHR^1$ with $R^1$ being an acetyl group and $X^2$ is —$NHR^1$ with $R^1$ being a C14 alkyl.

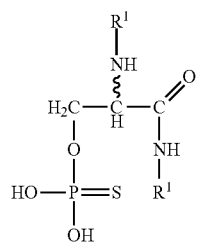

(III)

In the structures of formula (IV), $Q^1$ is =$NR^4$; $Q^2$ is $H_2$; $X^1$ and $X^2$ are linked together as —O—PO(OH)—O—; and $X^3$ is $R^1$—$Y^1$-A-, with A being a direct link and $Y^1$ being —NH—. $R^1$ and $R^4$ are as defined above for formula (I).

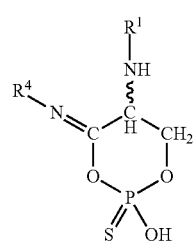

(IV)

In the structures of formulae (V)A and (V)B, $Q^1$ and $Q^2$ are both $H_2$; two of $X^1$, $X^2$, and $X^3$ are $(HO)_2PO$—$Z^1$—, with $Z^1$ being O for each; and one of $X^1$, $X^2$, and $X^3$ is $R^1$—$Y^1$-A-, with A being a direct link and $Y^1$ being —O—. $R^1$ is as defined above for formula (I). Preferred species within the scope of formulae (V)A and (V)B include the compounds where $R^1$ is an acyl including a C21 alkyl or where $R^1$ is a C18 alkyl.

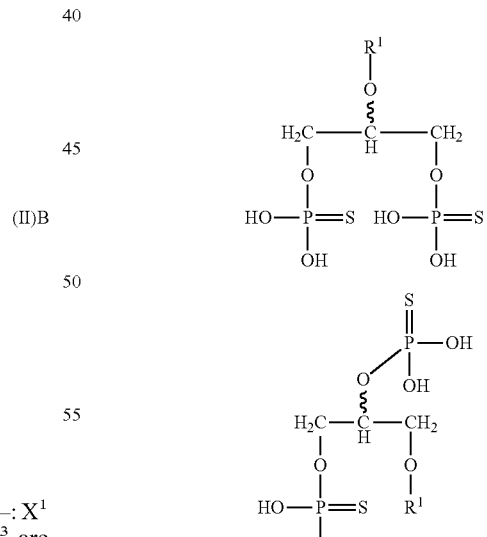

(V)A (V)B

The compounds according to formula (I), as well as the subgenus compounds according to formulae (II) A, (II) B, (III), (IV), (V) A, and (V) B, may be prepared using the synthesis schemes described in PCT/US01/08729, filed Mar. 19, 2001, (incorporated by reference in its entirety) except that phosphoramidate or pyrophosphates can be reacted in the presence of sulfur (with reflux) to obtain the thio-substituted derivatives.

In the compounds according to formula (VI), $Q^1$ and $Q^2$ are both $H_2$; one of $X^1$ and $X^2$ is $(HO)_2PS—Z^1—$, with $Z^1$ being O; and one of $X^1$, $X^2$, and $X^3$ is $R^1—Y^1$-A-, with A being a direct link and $Y^1$ being $—CH_2—$. $R^1$ is as defined above for formula (I). Preferred $R^1$ groups are saturated and unsaturated C2 to C24 hydrocarbons, both straight and branched chain, and arylakyl groups containing C2 to C24 hydrocarbons; most preferred $R^1$ groups are saturated and unsaturated C4 to C18 hydrocarbons. A preferred compound according to formula VI is thiophosphoric acid O-octadec-9-enyl ester (8g; also referred to as FAP 18:1d9).

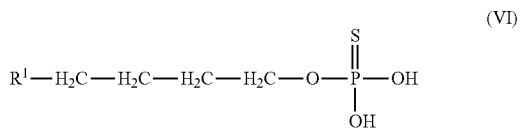

(VI)

The synthesis of thiophosphonates according to formula (VI) is outlined in scheme 2 of FIG. 1. The protected thiophosphoric acid O,O'-bis-(2-cyano-ethyl) ester O"-alkyl/alkenyl esters can be synthesized using a modified method of Haines et al. (1996). Commercially available fatty alcohols (6a-g) can be treated with a mixture of 1H-tetrazole and bis(2-cyanoethyl)-N,Ndiisopropyl phosphoramidite in anhydrous methylene chloride followed by reflux in the presence of elemental sulfur to give bis-cyanoethyl protected fatty alcohol thiophosphates (7a-g). These protected thiophosphates can be treated with methanolic KOH, followed by acidification to yield the required thiophosphates (8a-g).

In the structures of formulae (VII) A and (VII) B, $Q^1$ and $Q^2$ are both $H_2$; one of $X^1$, $X^2$, and $X^3$ is $(HO)_2PS—Z^1—$ with $Z^1$ being O; and two of $X^1$, $X^2$, and $X^3$ are $R^1—Y^1$-A-, with A being a direct link and $Y^1$ being O for each. Each $R^1$ is defined independently as above for formula (I).

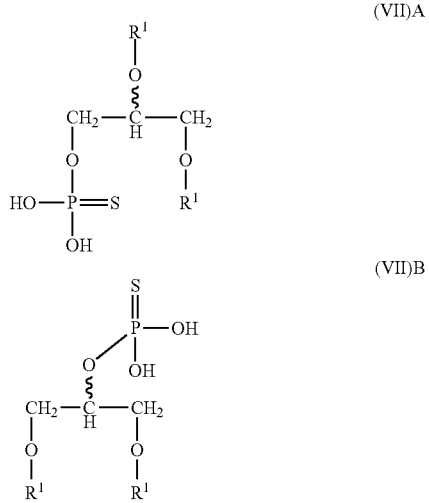

Preferred $R^1$ groups are saturated and unsaturated C6 to C24 hydrocarbons, both straight and branched chain; most preferred $R^1$ groups are saturated and unsaturated C8 to C18 hydrocarbons. Two preferred compounds according to group (VII) A are the (R) and (S) enantiomers where both $R^1$ groups are saturated octyl groups. The (R) enantiomer is a partial $LPA_1$ agonist ($EC_{50}$: 695 nM), a transient partial $LPA_2$ agonist ($EC_{50}$: 1.02 µM), and a full $LPA_3$ ($EC_{50}$: 3 nM) agonist. The (S) enantiomer is an agonist of the $LPA_1$ and $LPA_3$ receptors ($IC_{50}$ 328 nM for $LPA_1$ and $IC_{50}$ 184 nM for $LPA_3$ (both for 200 nM LPA)).

The compounds of formulae (VII) A and (VII) B can be prepared using the synthesis schemes described in PCT/US01/08729, filed Mar. 19, 2001, which is hereby incorporated by reference in its entirety, except that phosphoramidate can be reacted in the presence of sulfur (with reflux) to obtain the thio-substituted derivatives.

In the compounds according to formula (VIII), $Q^1$ and $Q^2$ are both $H_2$; one of $X^1$ and $X^2$ is $(HO)_2PS—Z^1—$, with $Z^1$ being $CF_2$; and one of $X^1$, $X^2$, and $X^3$ is $R^1—Y^1$-A-, with A being a direct link and $Y^1$ being $—CH_2—$. $R^1$ is as defined above for formula (I).

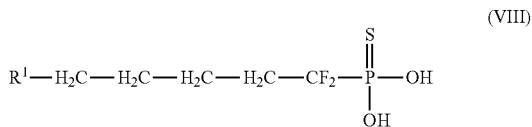

(VIII)

Preferred $R^1$ groups are saturated and unsaturated C2 to C20 hydrocarbons, both straight and branched chain; most preferred $R^1$ groups are saturated and unsaturated C4 to C12 hydrocarbons.

The synthesis of difluorothiophosphonates according to formula (VIII) is outlined in Scheme 3 of FIG. 1. The tetradecyl difluorophosphonate analog was synthesized in two steps (Scheme 3) using diethyl difluoromethanephosphonate as the starting material. Diethyl difluoromethanephosphonate was treated with LDA at −78° C. followed by reacting the anion with tetradecyl bromide to give the protected phosphonate 10. Compound 10 was deprotected using bromotrimethyl silane to yield the required difluorophosphonate compound (II).

Thus, the non-cyclic compounds of the present invention can be prepared by reacting $(Y^2O)_2PO—Z^{11}-Z^{13}$, $(Y^2O)_2PO—Z^{12}—P(OH)S—Z^{11}-Z^{13}$, where $Z^{11}$ is $—(CH_2)_m—$, $—CF_2—$, $—CF_2(CH_2)_m—$, or $—O(CH_2)_m—$ with m being an integer from 1 to 50, $—C(R^3)H—$, or $—O—$, $Z^{12}$ is $—(CH_2)_n—$ or $—O(CH_2)_n—$ with n being an integer from 1 to 50 or $—O—$, $Z^{13}$ is H or a first leaving group or $—Z^{11}-Z^{13}$ together to form the first leaving group, and $Y^2$ is H or a protecting group; with an intermediate compound according to formula (IX) in the presence of sulfur, followed by a de-protection step, if necessary, both performed under conditions effective to afford a compound according to formula (I) where one or two of $X^1$, $X^2$, and $X^3$ is $(HO)_2PS—Z^1—$ or $(HO)_2PS—Z^2—P(OH)S—Z^1—$ with $Z^1$ and $Z^2$ being defined as above.

The intermediate compound of formula (IX) has the following structure:

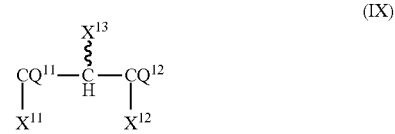

(IX)

wherein,
at least one of $X^{11}$, $X^{12}$, and $X^{13}$ is $R^{11}—Y^{11}$-A- with each being the same or different when two of $X^{11}$, $X^{12}$, and $X^{13}$ are $R^{11}—Y^{11}$-A-, or $X^{12}$ and $X^{13}$ are linked together as $—N(H)—C(O)—N(R^{11})—$;

at least one of $X^{11}$, $X^{12}$, and $X^{13}$ is OH, $NH_2$, SH, or a second leaving group;

optionally, one of $X^{11}$, $X^{12}$, and $X^{13}$ is H;

A is either a direct link, $(CH_2)_k$ with k being an integer from 0 to 30, or O;

$Y^{11}$ is —$(CH_2)_l$— with l being an integer from 1 to 30, —O—,

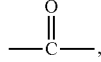

—S—, or $NR^{11}R^{12}$—;

$Q^1$ and $Q^2$ are independently $H_2$, =$NR^{13}$, =O, a combination of H and —$NR^{14}R^{15}$;

$R^{11}$, for each of $X^{11}$, $X^{12}$, or $X^{13}$, is independently hydrogen, a straight or branched-chain C1 to C30 alkyl, a straight or branched-chain C2 to C30 alkenyl, an aromatic or heteroaromatic ring with or without mono-, di-, or tri-substitutions of the ring, an acyl including a C1 to C30 alkyl or an aromatic or heteroaromatic ring, an arylalkyl including straight or branched-chain C1 to C30 alkyl, an aryloxyalkyl including straight or branched-chain C1 to C30 alkyl,

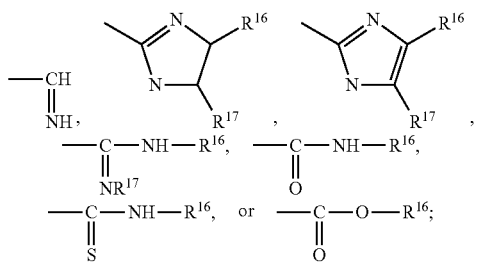

and $R^{12}$, $R^{13}$, $R^{14}$, $R^{15}$, $R^{16}$, and $R^{17}$ are independently hydrogen, a straight or branched-chain C1 to C30 alkyl, a straight or branched-chain C2 to C30 alkenyl, an aromatic or heteroaromatic ring with or without mono-, di-, or tri-substitutions of the ring, an acyl including a C1 to C30 alkyl or aromatic or heteroaromatic ring, an arylalkyl including straight or branched-chain C1 to C30 alkyl, or an aryloxyalkyl including straight or branched-chain C1 to C30 alkyl.

Having prepared the LPA receptor agonists and antagonists of the present invention, such compounds can be used to prepare pharmaceutical compositions suitable for treatment of patients as described hereinafter. Therefore, a further aspect of the present invention relates to a pharmaceutical composition that includes a pharmaceutically-acceptable carrier and a compound of the present invention. The pharmaceutical composition can also include suitable excipients, or stabilizers, and can be in solid or liquid form such as, tablets, capsules, powders, solutions, suspensions, or emulsions. Typically, the composition will contain from about 0.01 to 99 percent, preferably from about 20 to 75 percent of active compound(s), together with the carrier, excipient, stabilizer, etc.

The solid unit dosage forms can be of the conventional type. The solid form can be a capsule, such as an ordinary gelatin type containing the compounds of the present invention and a carrier, for example, lubricants and inert fillers such as, lactose, sucrose, or cornstarch. In another embodiment, these compounds are tableted with conventional tablet bases such as lactose, sucrose, or cornstarch in combination with binders like acacia, cornstarch, or gelatin, disintegrating agents, such as cornstarch, potato starch, or alginic acid, and a lubricant, like stearic acid or magnesium stearate.

The compounds of the present invention may also be administered in injectable or topically-applied dosages by solution or suspension of these materials in a physiologically acceptable diluent with a pharmaceutical carrier. Such carriers include sterile liquids, such as water and oils, with or without the addition of a surfactant and other pharmaceutically and physiologically acceptable carrier, including adjuvants, excipients or stabilizers. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions.

For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

Depending upon the treatment being effected, the compounds of the present invention can be administered orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes, such as, that of the nose, throat, and bronchial tubes.

Compositions within the scope of this invention include all compositions wherein the compound of the present invention is contained in an amount effective to achieve its intended purpose. While individual needs vary, determination of optimal ranges of effective amounts of each component is within the skill of the art. Typical dosages comprise about 0.01 to about 100 mg/kg body wt. The preferred dosages comprise about 0.1 to about 100 mg/kg body wt. The most preferred dosages comprise about 1 to about 100 mg/kg body wt. Treatment regimen for the administration of the compounds of the present invention can also be determined readily by those with ordinary skill in art.

Certain compounds of the present invention have been found to be useful as agonists of LPA receptors while other compounds of the present invention have been found useful as antagonists of LPA receptors. Due to their differences in activity, the various compounds find different uses. The preferred animal subject of the present invention is a mammal. The invention is particularly useful in the treatment of human subjects.

One aspect of the present invention relates to a method of modulating LPA receptor activity which includes providing a compound of the present invention which has activity as either an LPA receptor agonist or an LPA receptor antagonist and contacting an LPA receptor with the compound under conditions effective to modulate the activity of the LPA receptor.

LPA receptor agonists will characteristically induce LPA-like activity from an LPA receptor, which can be measured either chemically, e.g., $Ca^{2+}$ or $Cl^-$ current in oocytes, or by examining changes in cell morphology, mobility, proliferation, etc. In contrast, LPA receptor antagonists will characteristically block LPA-like activity from an LPA receptor. This too can be measured either chemically, e.g., $Ca^{2+}$ or $Cl^-$ current in oocytes, or by examining changes in cell morphology, mobility, proliferation, etc.

By virtue of the compounds of the present invention acting as LPA receptor antagonists, the present invention also relates to a method of inhibiting LPA-induced activity on an LPA receptor. This method includes providing a compound of the present invention which has activity as an LPA receptor antagonist and contacting an LPA receptor with the compound under conditions effective to inhibit LPA-induced activity of the LPA receptor. The LPA receptor is present on a cell which normally expresses the receptor or which heterologously expresses the receptor. The contacting of the LPA receptor with the compound of the present invention can be performed either in vitro or in vivo.

One aspect of the present invention relates to a method of treating cancer which includes providing a compound of the present invention and administering an effective amount of the compound to a patient in a manner effective to treat cancer. The types of cancer which can be treated with the compounds of the present invention include those cancers characterized by cancer cells whose behavior is attributable at least in part to LPA-mediated activity. Typically, these types of cancer are characterized by cancer cells which express one or more types of LPA receptors. Exemplary forms of cancer include, without limitation, prostate cancer, ovarian cancer, and bladder cancer.

The compounds of the present invention which are particularly useful for cancer treatment are the LPA receptor antagonists.

When administering the compounds of the present invention, they can be administered systemically or, alternatively, they can be administered directly to a specific site where cancer cells are present. Thus, administering can be accomplished in any manner effective for delivering the compound to cancer cells. LPA receptor antagonists, upon binding to LPA receptors, inhibit proliferation or metastasis of the cancer cells or destroy those cancer cells. Several LPA antagonist compounds synthesized by the inventors have been demonstrated to be cytotoxic to prostate cancer cell lines which express one or more LPA receptors of the type described above.

When the LPA antagonist compounds or pharmaceutical compositions of the present invention are administered to treat cancer, the pharmaceutical composition can also contain, or can be administered in conjunction with, other therapeutic agents or treatment regimen presently known or hereafter developed for the treatment of various types of cancer.

Cancer invasion is a complex multistep process in which individual cells or cell clusters detach from the primary tumor and reach the systemic circulation or the lymphatics to spread to different organs. Cancer cells require serum factors for their invasion, with LPA being an important serum component that is capable of restoring tumor cell invasive capability in serum-free systems.

Another aspect of the present invention relates to a method of enhancing cell proliferation. This method of enhancing cell proliferation includes the steps of providing a compound of the present invention which has activity as an agonist of an LPA receptor and contacting the LPA receptor on a cell with the compound in a manner effective to enhance LPA receptor-induced proliferation of the cell.

In addition to the roles that LPA plays in modulating cancer cell activity, there is strong evidence to suggest that LPA also has a physiological role in natural wound healing. At wound sites, LPA derived from activated platelets is believed to be responsible, at least in part, for stimulating cell proliferation at the site of injury and inflammation possibly in synchronization with other platelet-derived factors. LPA alone can stimulate platelet aggregation, which may in turn be the factor that initiates an element of positive feedback to the initial aggregatory response.

Due to the role of LPA in cell proliferation, compounds having LPA receptor agonist activity can be used in a manner effective to promote wound healing. Accordingly, another aspect of the present invention relates to a method of treating a wound. This method is carried out by providing a compound of the present invention which has activity as an agonist of an LPA receptor and delivering an effective amount of the compound to a wound site, where the compound binds to LPA receptors on cells that promote healing of the wound, thereby stimulating LPA receptor agonist-induced cell proliferation to promote wound healing.

The compounds of the present invention which are effective in wound healing can also be administered in combination, i.e., in the pharmaceutical composition of the present invention or simultaneously administered via different routes, with a medicament selected from the group consisting of an antibacterial agent, an antiviral agent, an antifungal agent, an antiparasitic agent, an antiinflammatory agent, an analgesic agent, an antipruritic agent, or a combination thereof.

For wound healing, a preferred mode of administration is by the topical route. However, alternatively, or concurrently, the agent may be administered by parenteral, subcutaneous, intravenous, intramuscular, intraperitoneal or transdermal routes. Alternatively, or concurrently, administration may be by the oral route. The dosage administered will be dependent upon the age, health, and weight of the recipient, kind of concurrent treatment, if any, frequency of treatment, and the nature of the effect desired.

For the preferred topical applications, especially for treatment of humans and animals having a wound, it is preferred to administer an effective amount of a compound according to the present invention to the wounded area, e.g., skin surfaces. This amount will generally range from about 0.001 mg to about 1 g per application, depending upon the area to be treated, the severity of the symptoms, and the nature of the topical vehicle employed. A preferred topical preparation is an ointment wherein about 0.01 to about 50 mg of active ingredient is used per ml of ointment base, such as PEG-1000.

The present invention further provides methods of inhibiting apoptosis or preserving or restoring cell, tissue or organ function. This method is carried out by providing a compound of the present invention which has activity as an agonist of an LPA receptor and contacting a cell, tissue, or organ with an amount of the compound which is effective to inhibit apoptosis, or preserve or restore function in the cell, tissue, or organ. The contacting can be carried out in vitro (i.e., during cell culture or organ or tissue transfer) or in vivo (i.e., by administering the effective amount of the compound to a patient as indicated below).

Various indications which can be treated, include, but are not limited to, those related to apoptosis, ischemia, traumatic injury, and reperfusion damage. Those conditions related to apoptosis include, but are not limited to, dermatological effects of aging, the effects of reperfusion after an ischemic event, immunosuppression, gastrointestinal perturbations, cardiovascular disorders, rejection of tissue transplantation, wound healing, and Alzheimer's disease. The treatment can also diminish the apoptosis-related problems associated with viral infection, chemotherapeutic agents, radiation, and immunosuppressive drugs. These stimuli trigger apoptosis in a variety of disorders, including, but not limited to, those of the digestive tract tissues.

A preferred compound for practicing this aspect of the present invention is compound 8g, particularly with respect to the protection of tissues such as those of the gastrointestinal and hematopoietic systems against chemotherapeutic- or radiation-induced apoptosis as described in the Examples herein.

The treatments are also suitable during all phases of organ transplantation. The compounds having agonist activity on an LPA receptor can be used to prepare the organ by administering an amount of the compound to the donor effective to stabilize or preserve the organ. The organ can be perfused and/or preserved in OPS containing the compound. The organ recipient can then be administered an amount of the compound effective to enhance organ stability and function. The compositions are also particularly suitable for use in treating cardioplegia, whether related to transplantation or other surgical intervention.

Gastrointestinal tissue damage includes, but is not limited to, damage to the lining of the gut, severe chronic ulcers, colitis, radiation induced damage, chemotherapy induced damage, and the perturbation of the gastrointestinal tract caused by parasites, and diarrhea from any other cause. Various viral and bacterial infections are known to result in gastrointestinal perturbations. The compounds having agonist activity on an LPA receptor are also suitable for use in treatment of the side effects associated with these infections. Such compounds are particularly suited for use in ameliorating the gastrointestinal disturbances associated with chemotherapy. Thus, such compounds are suitable for use not only in preventing the diarrhea associated with chemotherapy but also the nausea.

These compounds are particularly suited to treatment of various gastrointestinal conditions in animals, including, but not limited to livestock and domesticated animals. Such conditions, particularly diarrhea, account for the loss of many calves and puppies to dehydration and malnutrition. Treatment of gastrointestinal conditions is preferably by gastrointestinal administration. In the case of cattle and domesticated animals, an effective amount of these compounds can be conveniently mixed in with the feed. In humans, administration can be by any method known in the art of gastrointestinal administration. Preferably, administration is oral.

In addition, the compounds having agonist activity on an LPA receptor can be administered to immunodeficient patients, particularly HIV-positive patients, to prevent or at least mitigate apoptotic death of T cells associated with the condition, which results in the exacerbation of immunodeficiencies as seen in patients with AIDS. The compounds having agonist activity on an LPA receptor can also be administered to treat apoptosis associated with reperfusion damage involved in a variety of conditions, including, but not limited to, coronary artery obstruction; cerebral infarction; spinal/head trauma and concomitant severe paralysis; reperfusion damage due to other insults such as frostbite, coronary angioplasty, blood vessel attachment, limb attachment, organ attachment and kidney reperfusion.

Myocardial and cerebral infarctions (stroke) are caused generally by a sudden insufficiency of arterial or venous blood supply due to emboli, thrombi, or pressure that produces a macroscopic area of necrosis; the heart, brain, spleen, kidney, intestine, lung and testes are likely to be affected. Cell death occurs in tissue surrounding the infarct upon reperfusion of blood to the area; thus, the compositions are effective if administered at the onset of the infarct, during reperfusion, or shortly thereafter. The present invention includes methods of treating reperfusion damage by administering a therapeutically effective amount of the compounds having agonist activity on an LPA receptor to a patient in need of such therapy.

The invention further encompasses a method of reducing the damage associated with myocardial and cerebral infarctions for patients with a high risk of heart attack and stroke by administering a therapeutically effective amount of the compounds having agonist activity on an LPA receptor to a patient in need of such therapy. Preferably, treatment of such damage is by parenteral administration of such compounds. Any other suitable method can be used, however, for instance, direct cardiac injection in the case of myocardial infarct. Devices for such injection are known in the art, for instance the Aboject cardiac syringe.

The invention further provides methods of limiting and preventing apoptosis in cells, or otherwise preserving cells, during the culture or maintenance of mammalian organs, tissues, and cells, by the addition of an effective amount of the compounds having agonist activity on an LPA receptor to any media or solutions used in the art of culturing or maintaining mammalian organs, tissues, and cells.

The invention further encompasses media and solutions known in the art of culturing and maintaining mammalian organs, tissues and cells, which include an amount of the compounds having agonist activity on an LPA receptor which is effective to preserve or restore cell, tissue or organ function, or limit or prevent apoptosis of the cells in culture. These aspects of the invention encompass mammalian cell culture media including an effective amount of at least one compounds having agonist activity on an LPA receptor and the use of such media to preserve or restore cell, tissue or organ function, or to limit or prevent apoptosis in mammalian cell culture. An effective amount is one which decreases the rate of apoptosis and/or preserves the cells, tissue or organ. Such compounds can limit or prevent apoptosis under circumstances in which cells are subjected to mild traumas which would normally stimulate apoptosis. Exemplary traumas can include, but are not limited to, low level irradiation, thawing of frozen cell stocks, rapid changes in the temperature, pH, osmolarity, or ion concentration of culture media, prolonged exposure to non-optimal temperature, pH, osmolarity, or ion concentration of the culture media, exposure to cytotoxins, disassociation of cells from an intact tissue in the preparation of primary cell cultures, and serum deprivation (or growth in serum-free media).

The invention encompasses compositions comprising tissue culture medium and an effective amount of the compounds having agonist activity on an LPA receptor. The invention further encompasses solutions for maintaining mammalian organs prior to transplantation, which solutions include an effective amount of the compounds having agonist activity on an LPA receptor, and the use of such solutions to preserve or restore organ function or to limit or prevent apoptosis in treated mammalian organs during their surgical removal and handling prior to transplantation. The solutions can be used to rush, perfuse and/or store the organs. In all cases, concentrations of the compounds (having agonist activity on an LPA receptor) required to limit or prevent damage to the organs can be determined empirically by one skilled in the art by methods known in the art.

In addition to the foregoing, the compounds having agonist activity on an LPA receptor can be topically applied to the skin to treat a variety of dermatologic conditions. These conditions include, but are not limited to, hair loss and wrinkling due to age and/or photo damage. The present invention also encompasses, therefore, methods of treating dermatological conditions. The various dermatologic conditions are preferably treated by topical application of an effective amount of a compound having agonist activity on an LPA receptor (or compositions which contain them). An effective amount of such compounds is one which ameliorates or diminishes the symptoms of the dermatologic conditions. Preferably, the treatment results in resolution of the dermatologic condition or restoration of normal skin function; however, any amelioration or lessening of symptoms is encompassed by the invention.

EXAMPLES

The following examples are intended to illustrate, but not limit, the scope of the present invention as set forth in the appended claims.

General Methods

All reagents were purchased from Sigma-Aldrich Chemical Co., Fisher Scientific (Pittsburgh, Pa.), Bedukian Research (Danbury, Conn.) and Toronto Research Chemicals (North York, ON, Canada) and were used without further purification. Phosphonate analogs were purchased from Lancaster (Pelham, N.H.; n-decyl-phosphonate (9a)), PolyCarbon (Devens, Mass.; n-dodecyl-phosphonate (9b)), Alfa Aesar (Ward Hill, Mass.; n-tetradecyl-phosphonate (9c) and n-octadecyl-phosphonate (9d)). LPA 18:1, DGPP, Ser-PA, and Tyr-PA were obtained from Avanti Polar Lipids (Alabaster, Ala.). Melting points were determined on a Thomas-Hoover capillary melting point apparatus and are uncorrected. Routine thin-layer chromatography (TLC) was performed on 250 μM glassbacked UNIPLATES (Analtech, Newark, Del.). Flash chromatography was performed on prepacked silica gel columns using a Horizon HPFC system (Biotage, Charlottesville, Va.). $^1$H and $^{31}$P NMR spectra were obtained on a Bruker AX 300 (Billerica, Mass.) spectrometer. Chemical shifts for $^1$H NMR are reported as parts per million (ppm) relative to TMS. Chemical shifts for $^{31}$P NMR are reported as parts per million (ppm) relative to 0.0485 M triphenylphosphate in $CDCl_3$. Mass spectral data was collected on a Bruker ESQUIRE electrospray/ion trap instrument in the positive and negative ion modes. Elemental analyses were performed by Atlantic Microlab Inc., Norcross, Ga.

Example 1

Synthesis of Phosphoric Acid di-tert-butyl Ester Alkenyl Esters (4a-f)

Commercially available unsaturated fatty alcohols (3a-f) were used as starting materials. To a stirred solution of alcohol (2.5 mmol) and di-tert-butyl-N,N-diisopropyl phosphoramidite (1.51 g, 4 mmol) in methylene chloride (60 mL) was added 1H-tetrazole (578 mg, 8.25 mmol). After 30 minutes of stirring the mixture was cooled to 0° C. and 0.3 mL of 50% hydrogen peroxide was added. The mixture was stirred for 1 h., diluted with methylene chloride (100 mL), washed with 10% sodium metabisulfite (2×50 ml), saturated sodium bicarbonate (2×50 ml), water (50 ml), and brine (50 ml). The organic layer was dried over anhydrous sodium sulfate, filtered, and concentrated under vacuum. The resulting crude products were purified by silica gel chromatography using hexane/ethyl acetate (7:3) to elute the desired products, di-t-Boc protected fatty alcohol phosphates (4a-f).

Phosphoric acid di-tert-butyl ester dec-9-enyl ester (4a): Isolated as clear oil (75% yield). $^1$H NMR ($CDCl_3$): δ5.80 (m, 1H), 4.95 (m, 2H), 3.95 (q, J=7.5 Hz, 2H), 2.03 (q, J=7.1 Hz, 2H), 1.65 (quintet, 2H), 1.48 (s, 18H), 1.30 (br s, 10H); $^{31}$P NMR ($CDCl_3$): δ7.90; MS: [M+$^{23}$Na] at m/z 371.3.

Phosphoric acid di-tert-butyl ester dec-4-enyl ester (4b): Isolated as clear oil (68% yield). $^1$H NMR ($CDCl_3$): δ5.25 (m, 2H), 3.84 (q, J=6.8 Hz, 2H), 2.05 (q, J=7.0 Hz, 2H), 1.98 (q, J=6.8 Hz, 2H), 1.61 (quintet, 2H), 1.42 (s, 18H), 1.22 (br s, 6H), 0.80 (t, J=7.2 Hz, 3H); $^{31}$P NMR (MeOH-$d_4$): δ7.90; MS: [M+$^{23}$Na] at m/z 371.3.

Phosphoric acid di-tert-butyl ester dodec-9-enyl ester (4c): Isolated as clear oil (70% yield). $^1$H NMR ($CDCl_3$): δ5.26 (m, 2H), 3.88 (q, J=6.6 Hz, 2H), 1.94 (m, 4H), 1.59 (quintet, 2H), 1.42 (s, 18H), 1.24 (br s, 10H), 0.89 (t, J=7.5 Hz, 3H); $^{31}$P NMR ($CDCl_3$): δ7.80; MS: [M+$^{23}$Na] at m/z 399.5.

Phosphoric acid di-tert-butyl ester tetradec-9-enyl ester (4d): Isolated as clear oil (68% yield). $^1$H NMR ($CDCl_3$): δ5.34 (t, J=5.2 Hz, 2H), 3.94 (q, J=6.6 Hz, 2H), 2.01 (m, 4H), 1.65 (quintet, 2H), 1.48 (s, 18H), 1.30 (br s, 18H), 0.90 (t, J=7.4 Hz, 3H); $^{31}$P NMR ($CDCl_3$): δ7.90; MS: [M+$^{23}$Na] at m/z 427.4.

Phosphoric acid di-tert-butyl ester tetradec-11-enyl ester (4e): Isolated as clear oil (82% yield). $^1$H NMR ($CDCl_3$): δ5.34 (m, 2H), 3.94 (q, J=6.5 Hz, 2H), 2.01 (m, 4H), 1.65 (quintet, 2H), 1.48 (s, 18H), 1.23 (br s, 14H), 0.95 (t, J=7.4 Hz, 3H); $^{31}$P NMR ($CDCl_3$): δ8.10; MS: [M+$^{23}$Na] at m/z 427.4.

Phosphoric acid di-tert-butyl ester octadec-9-enyl ester (4f): Isolated as clear oil (72% yield). $^1$H NMR ($CDCl_3$): δ5.34 (m, 2H), 3.94 (q, J=6.9 Hz, 2H), 2.01 (m, 4H), 1.66 (quintet, 2H), 1.48 (s, 18H), 1.28 (br s, 22H), 0.88 (t, J=6.6 Hz, 3H); $^{31}$P NMR ($CDCl_3$): δ8.10; MS: [M+$^{23}$Na] at m/z 483.5.

Example 2

Synthesis of Phosphoric Acid Mono Alkenyl Esters (5a-f)

The Boc-protected FAPs (4a-f) were deprotected with TFA to yield the corresponding unsaturated FAPs (5a-f). To a solution of 100 mg of 1a-6a in methylene chloride (20 mL), trifluoroacetic acid (0.3 mL) was added. The mixture was allowed to stir for 4 h., and TLC showed the completion of the reaction. Solvents were evaporated; the residue was washed with methylene chloride (2×20 mL), and concentrated under vacuum to yield the desired phosphoric acid mono alkenyl esters as colorless oils.

Phosphoric acid monodec-9-enyl ester (5a): Isolated as an oil (85%). $^1$H NMR (MeOH-$d_4$): δ5.74 (m, 1H), 4.88 (m, 2H), 3.90 (q, J=6.6 Hz, 2H), 2.01 (q, J=6.9 Hz, 2H), 1.61 (quintet, 2H), 1.28 (br s, 10H); $^{31}$P NMR (MeOH-$d_4$): δ17.84; MS: [M−H]− at m/z 235.2. Anal. ($C_{10}H_{21}O_4P \cdot 0.1H_2O$) C, H.

Phosphoric acid monodec-4-enyl ester (5b): Isolated as an oil (78%). $^1$H NMR (MeOH-$d_4$): δ5.31 (m, 2H), 3.84 (q, J=6.8 Hz, 2H), 2.05 (q, J=7.0 Hz, 2H), 1.98 (q, J=6.8 Hz, 2H), 1.61 (quintet, 2H), 1.22 (br s, 6H), 0.80 (t, J=7.2 Hz, 3H); $^{31}$P NMR (MeOH-$d_4$): δ17.45; MS: [M−H]− at m/z 235.2. Anal. ($C_{10}H_{21}O_4P \cdot 0.5H_2O$) C, H.

Phosphoric acid monododec-9-enyl ester (5c): Isolated as an oil (82%).

$^1$H NMR (DMSO/MeOH-$d_4$): δ5.28 (m, 2H), 3.82 (q, J=6.6 Hz, 2H), 1.96 (m, 4H), 1.54 (m, 2H), 1.25 (br s, 10H), 0.88 (t, J=7.2 Hz, 3H); $^{31}$P NMR (MeOH-$d_4$): Δ16.22; MS: [M−H]− at m/z 263.0. Anal. ($C_{12}H_{25}O_4P \cdot 0.6H_2O$) C, H.

Phosphoric acid monotetradec-9-enyl ester (5d): Isolated as an oil (84%). $^1$H NMR ($CDCl_3$/MeOH-$d_4$): δ5.21 (m, 2H), 3.84 (q, J=6.5 Hz, 2H), 1.91 (m, 4H), 1.54 (m, 2H), 1.20 (br s, 14H), 0.78 (m, 3H); $^{31}$P NMR (MeOH-$d_4$): Δ16.20; MS: [M−H]− at m/z 291.4. Anal. ($C_{14}H_{29}O_4P \cdot 0.25H_2O$) C, H.

Phosphoric acid monotetradec-11-enyl ester (5e): Isolated as an oil (78%). $^1$H NMR (MeOH-d$_4$): δ5.24 (m, 2H), 3.88 (q, J=6.6 Hz, 2H), 1.95 (m, 4H), 1.58 (m, 2H), 1.25 (br s, 14H), 0.86 (t, J=7.1 Hz, 3H); $^{31}$P NMR (MeOH-d$_4$): δ16.20; MS: [M−H]− at m/z 291.3. Anal. (C$_{14}$H$_{29}$O$_4$P)C, H.

Phosphoric acid monooctadec-9-enyl ester (5f): Isolated as an oil (86%). $^1$HNMR (MeOH-d$_4$): δ5.30 (m, 2H), 3.91 (q, J=6.6 Hz, 2H), 2.00 (m, 4H), 1.62 (quintet, 2H), 1.26 (br s, 22H), 0.86 (t, J=6.0 Hz, 3H); $^{31}$p NMR (MeOH-d$_4$): δ16.21; MS: [M−H]− at m/z 347.4. Anal. (C$_{18}$H$_{37}$O$_4$P.0.4H$_2$O)C, H.

Example 3

Synthesis of Thiophosphoric Acid O,O'-bis-(2-cyano-ethyl) Ester O''-alkyl/alkenyl Esters (7a-g)

Commercially available saturated or unsaturated fatty alcohols (6a-g) were used as starting materials. A solution of alcohol (2.0 mmol), bis-(2-cyanoethyl)-N,N-diisopropyl phosphoramidite (1.085 g, 4 mmol) and 1H-tetrazole (420 mg, 6 mmol) was stirred for 30 minutes at room temperature, followed by the addition of elemental sulfur (200 mg) and the mixture was refluxed for 2 h. The reaction mixture was cooled to room temperature and solvents were evaporated under vacuum. Addition of ethyl acetate (30 mL) precipitated excess sulfur, which was filtered out, and the solvent was evaporated to give the crude mixture. The mixture was purified by flash chromatography to give the desired products as colorless oils.

Thiophosphoric acid O,O'-bis-(2-cyano-ethyl) ester O''-decyl ester (7a): Isolated as colorless oil (72% yield). $^1$H NMR (CDCl$_3$): δ4.21-4.35 (m, 4H), 4.12 (m, 2H), 2.8 (t, J=6.3 Hz, 4H), 1.68 (quintet, 2H), 1.26 (br s, 14H), 0.88 (t, J=6.0 Hz, 3H); MS: [M+$^{23}$Na] at m/z 383.4.

Thiophosphoric acid O,O'-bis-(2-cyano-ethyl) ester O''-dodecyl ester (7b): Isolated as colorless oil (84% yield). $^1$H NMR (CDCl$_3$): δ4.26-4.33 (m, 4H), 4.12 (m, 2H), 2.8 (t, J=6.2 Hz, 4H), 1.71 (quintet, 2H), 1.26 (br s, 14H), 0.88 (t, J=6.6 Hz, 3H); MS: [M+$^{23}$Na] at m/z 411.4.

Thiophosphoric acid O,O'-bis-(2-cyano-ethyl) ester O''-tetradecyl ester (7c): Isolated as clear oil (82% yield). $^1$HNMR (CDCl$_3$): δ4.25-4.33 (m, 4H), 4.12 (m, 2H), 2.8 (t, J=6.0 Hz, 4H), 1.71 (quintet, 2H), 1.26 (br s, 18H), 0.88 (t, J=6.6 Hz, 3H); MS: [M+$^{23}$Na] at m/z 439.5.

Thiophosphoric acid O,O'-bis-(2-cyano-ethyl) ester O''-dec-9-enyl ester (7d): Isolated as clear oil (76% yield). $^1$H NMR (CDCl$_3$): δ5.81 (m, 1H), 4.96 (m, 2H), 4.22-4.32 (m, 4H), 4.11 (m, 2H), 2.8 (t, J=6.3 Hz, 4H), 2.01 (t, J=6.6 Hz, 4H), 1.70 (quintet, 2H), 1.31 (br s, 10H); MS: [M+$^{23}$Na] at m/z 381.3.

Thiophosphoric acid O,O-bis-(2-cyano-ethyl) ester O''-dodec-9-enyl ester (7e): Isolated as clear oil (80% yield). $^1$H NMR (CDCl$_3$): δ5.34 (m, 2H), 4.25-4.33 (m, 4H), 4.11 (m, 2H), 2.8 (t, J=6.0 Hz, 4H), 2.07 (m, 2H), 1.70 (quintet, 2H), 1.31 (br s, 10H), 0.96 (t, J=7.5 Hz, 3H); MS: [M+$^{23}$Na] at m/z 409.5.

Thiophosphoric acid O,O'-bis-(2-cyano-ethyl) ester O''-tetradec-9-enyl ester (7f): Isolated as clear oil (75% yield). $^1$H NMR (CDCl$_3$): δ5.35 (m, 2H), 4.25-4.33 (m, H), 4.12 (m, 2H), 2.78 (t, J=6.0 Hz, 4H), 2.02 (m, 2H), 1.71 (quintet, 2H), 1.31 (br s, 14H), 0.90 (t, J=7.2 Hz, 3H); MS: [M+$^{23}$Na] at m/z 437.5.

Thiophosphoric acid O,O'-bis-(2-cyano-ethyl) ester O''-octadec-9-enyl ester (7g): Isolated as clear oil (72% yield). $^1$H NMR (CDCl$_3$): δ5.35 (m, 2H), 4.27-4.31 (m, 4H), 4.12 (m, 2H), 2.78 (t, J=6.0 Hz, 4H), 2.02 (m, 2H), 1.71 (quintet, 2H), 1.27 (br s, 22H), 0.88 (t, J=7.2 Hz, 3H); MS: [M+$^{23}$Na] at m/z 493.5.

Example 4

Synthesis of Thiophosphoric Acid O-alkyl/alkenyl Esters (8a-g)

Thiophosphoric acid O,O'-bis-(2-cyano-ethyl) ester O''-alkyl/alkenyl esters (7a-7g) were used as starting materials. A solution of 100 mg of 7a-7g in methanolic KOH (10 mL) was stirred for 2 h., and TLC showed the completion of the reaction. The solvent was evaporated to give the crude product, which was dissolved in water (20 mL), and acidified with HCl. The aqueous mixture was extracted with ethyl acetate (2×50 mL), organic layer was dried over sodium sulfate and concentrated under vacuum to give the desired compound as light yellow colored oil.

Thiophosphoric acid O-decyl ester (8a): Isolated as light yellow colored oil (80% yield). $^1$H NMR (DMSO): 83.86 (m, 2H), 1.56 (quintet, 2H), 1.24 (br s, 14H), 0.86 (t, J=6.0 Hz, 3H); MS: [M−H]− at m/z 253.2. Anal. (C$_{10}$H$_{23}$O$_3$PS)C, H.

Thiophosphoric acid O-dodecyl ester (8b): Isolated as light yellow colored oil (73% yield). $^1$H NMR (DMSO): 83.84 (m, 2H), 1.56 (quintet, 2H), 1.24 (br s, 18H), 0.83 (t, J=6.9 Hz, 3H); MS: [M−H]− at m/z 280.9. Anal. (C$_{12}$H$_{27}$O$_3$PS.0.5H$_2$O)C, H.

Thiophosphoric acid O-tetradecyl ester (8c): Isolated as light yellow colored oil (70% yield). $^1$H NMR (DMSO): 83.85 (m, 2-1), 1.56 (quintet, 2H), 1.24 (br s, 22H), 0.85 (t, J=6.0 Hz, 3H); MS: [M−H]− at m/z 309.4. Anal. (C$_{14}$H$_{31}$O$_3$PS.0.25H$_2$O)C, H.

Thiophosphoric acid O-dec-9-enyl ester (8d): Isolated as light yellow colored oil (76% yield). $^1$H NMR (DMSO): 85.79 (m, 1H), 4.94 (m, 2H), 3.85 (m, 2H), 2.01 (q, J=6.6 Hz, 4H), 1.55 (quintet, 2H), 1.26 (br s, 10H); MS: [M−H]− at m/z 251.1. Anal. (C$_{10}$H$_{21}$O$_3$PS)C, H.

Thiophosphoric acid O-dodec-9-enyl ester (8e): Isolated as light yellow colored oil (80% yield). $^1$H NMR (DMSO): A 5.31 (m, 2H), 3.85 (q, J=6.6 Hz, 2H), 1.99 (m, 4H), 1.56 (quintet, 2H), 1.26 (br s, 10H), 0.91 (t, J=7.5 Hz, 3H); MS: [M−H]− at m/z 279.5. Anal. (C$_{12}$H$_{25}$O$_3$PS0.35H$_2$O)C, H.

Thiophosphoric acid O-tetradec-9-enyl ester (80: Isolated as light yellow colored oil (72% yield). $^1$H NMR (DMSO): 85.32 (m, 2H), 3.85 (m, 2H), 1.98 (m, 4H), 1.55 (quintet, 2H), 1.26 (br s, 14H), 0.86 (t, J=6.9 Hz, 3H); MS: [M−H]− at m/z 307.5. Anal. (C$_{14}$H$_{29}$O$_3$PS.0.3H$_2$O)C, H.

Thiophosphoric acid O-octadec-9-enyl ester (8g): Isolated as light yellow colored oil (82% yield). $^1$H NMR (DMSO): 85.32 (m, 2H), 3.85 (m, 2H), 1.97 (m, 4H), 1.55 (quintet, 2H), 1.24 (br s, 22H), 0.85 (t, J=6.9 Hz, 3H); MS: [M−H]− at m/z 363.5. Anal. (C$_{18}$H$_{37}$O$_3$PS.0.3H$_2$O)C, H.

Example 5

Synthesis of (1,1-Difluoro-pentadecyl) Phosphonic Acid Diethyl Ester (10)

To a solution of diethyl difluoromethanephosphonate (1.0 g, 5.316 mmol) in THF (50 mL) 2 M LDA (626 mg, 5.847 mmol) was added at −78° C. and stirred for 30 min. Tetradecyl bromide (1.474 g, 5.316 mmol) in THF (10 mL) was added to the mixture at −78° C. and the reaction mixture was stirred overnight. THF was evaporated and the residual oil was purified by flash chromatography using 30% ethyl acetate in hexane as eluent to give 817 mg (40%) of compound 10 as colorless oil. $^1$H NMR (CDCl$_3$): δ4.26 (m, 4H), 2.05 (m, 2H), 1.56 (m, 2H), 1.37 (t, J=6.9 Hz, 6H), 1.25 (br s, 22H), 0.87 (t, J=6.6 Hz, 3H); MS: [M+$^{23}$Na] at m/z 407.2.

Example 6

Synthesis of (1,1-Difluoro-pentadecyl) Phosphonic Acid (11)

To a solution of vacuum dried 10 (225 mg, 0.585 mmol) in methylene chloride (5 mL) bromotrimethyl silane (895 mg, 5.85 mmol) was added and the mixture was stirred at room temperature. TLC showed completion of the reaction after 6 h. Solvents were removed under reduced pressure, and the residue was stirred in 95% methanol (3 mL) for 1 h. The mixture was concentrated under reduced pressure, dried under vacuum to give 150 mg (78%) of 11 as light yellow solid. mp 66-69° C.; $_1$H NMR (CD$_3$OD): δ2.03 (m, 2H), 1.59 (m, 2H), 1.24 (br s, 22H), 0.90 (t, J=6.6 Hz, 3H); MS: [M–H]– at m/z 327.3. Anal. (C$_{15}$H$_3$]F$_2$O$_3$P.0.2H$_2$O)C, H.

Example 7

Analysis of Compounds for LPA Receptor Agonist or Antagonist Activity

Compounds were tested for their ability to induce or inhibit LPA-induced calcium transients in RH7777 rat hepatoma cells stably expressing LPA$_1$, LPA$_2$, and LPA$_3$ receptors and in PC-3 that express LPA$_{1-3}$ endogenously, using a FlexStation II automated fluorometer (Molecular Devices, Sunnyvale, Calif.).

RH7777 cells stably expressing either LPA$_1$, LPA$_2$ or LPA$_3$ or PC-3 cells were plated on poly-D lysine-coated black wall clear bottom 96-well plates (Becton Dickinson, San Jose, Calif.) with a density of 50000 cells/well, and cultured overnight. The culture medium (DMEM containing 10% FBS) was then replaced with modified Krebs solution (120 mM NaCl, 5 mM KCl, 0.62 mM MgSO$_4$, 1.8 mM CaCl$_2$, 10 mM HEPES, 6 mM glucose, pH 7.4) and the cells were serum starved for 6-8 hours (12 h for PC-3 cells). Cells were loaded with Fura-2 AM for 35 minutes in modified Krebs medium. The Fura-2 was removed before loading the plate in the FlexStation instrument by replacing the medium once again with 100 μl modified Krebs medium/well. Plates were incubated for 4 minutes in the instrument to allow for warming to 37° C. Changes in intracellular Ca$^{2+}$ concentration were monitored by measuring the ratio of emitted light intensity at 520 nm in response to excitation by 340 nm and 380 nm wavelength lights, respectively. Each well was monitored for 80-120 seconds. 50 μl of the test compound (3× stock solution in modified Krebs) was added automatically to each well 15 seconds after the start of the measurement. Time courses were recorded using the SoftMax Pro software (Molecular Devices, Sunnyvale, Calif.). Ca$^+$ transients were quantified automatically by calculating the difference between maximum and baseline ratio values for each well.

Selected compounds were tested for PPARγ activation in CV1 cells, transfected with an acyl-coenzyme A oxidase-luciferase (PPRE-Acox-Rluc) reporter gene construct. Briefly, CV-1 cells were plated in 96-well plates (5×10$_3$ cells per well) in Dulbecco's modified Eagle's medium supplemented with 10% fetal bovine serum. The next day, the cells were transiently transfected with 125 ng of pGL3-PPRE-Acox-Rluc, 62.5 ng of pcDNAI-PPARγ, and 12.5 ng of pSV-β-galactosidase (Promega, Madison, Wis.) using LipofectAMINE 2000 (Invitrogen). Twenty-four hours after System (Promega) and the Galacto-Light Plus™ System (Applied Biosystems, Foster City, Calif.), respectively, samples were run in quadruplicate and the mean±standard errors were calculated. Data are representative of at least two independent transfections. Student's t-test was used for null hypothesis testing and P<0.05 was considered transfection, cells were treated with 1% FBS supplemented OptiMEMI (Invitrogen) containing DMSO or 10 μM test compound dissolved in DMSO for 20 h. Luciferase and β-galactosidase activities were measured with the Steady-Glo® Luciferase Assay as significant.

A series of FAP analogs with an unsaturation at different positions in the sidechain (5a-f), thiophosphates (8a-g) and phosphonates (9ad, 11) were synthesized. These new analogs were evaluated as agonists and antagonists with respect to LPA$_{1-3}$. Each FAP analog was tested for the ability to induce Ca$^{2+}$ transients in RH7777 cells transfected with LPA$_{1-3}$ receptors (agonism), as well as the ability to inhibit LPA-induced Ca$^{2+}$ transients in the same cells (antagonism). None of the compounds examined in this study induced intracellular Ca$^{2+}$ transients when applied up to a concentration of 30 μM in non-transfected RH7777 cells. The effects of unsaturation at different positions, modification of head group by phosphonate, difluoro phosphonate and thiophosphate with/ without unsaturation dramatically changed the pharmacological properties of FAPs on LPA$_{1-3}$ receptors. The mono-unsaturated FAP analogs (5a-e) showed a trend of increasing the potency and/or efficacy when compared to the saturated analogs, except C-10 analogs, without changing their ligand properties as agonists or antagonists at the LPA$_2$ and LPA$_3$ receptors. The position of the double bond also had an impact on the activity. Comparison of the activities between decenyl regio isomers 5a and 5b, suggests that the C$_9$=C$_{10}$ double bond, as found in LPA 18:1, was preferred over C$_4$=C$_5$ in activating LPA$_2$ receptor (EC$_{50}$=3800 nM for 5a versus >10000 nM for 5b). Though 5b (K$_i$=370 nM) was moderately more active than 5a (K$_i$=504 nM), the preference for the double bond position was much less pronounced for inhibition of LPA$_3$ receptor.

Similarly, the LPA$_2$ receptor showed preference for C$_9$=C$_{10}$ unsaturation between the tetradecenyl isomers 5d (EC$_{50}$=397 nM) and 5e (EC$_{50}$=4100 nM), and LPA$_3$ showed no significant preference for double bond position. In contrast, LPA$_1$ preferred C$_{11}$=C$_{12}$ over C$_9$=C$_{10}$ between 5d (K$_i$=1146 nM) and 5e (K$_i$=457 nM), indicating the possibility of a differential conformational requirement in the side chain for each of the three LPA receptors. In the unsaturated series, only tetradecenyl compounds (5d, 5e) antagonized the LPA response at LPA$_1$ receptor.

The replacement of phosphate with a thiophosphate as the headgroup in 10-, 12-, and 14-carbon saturated FAP analogs (8a-c) had a significant impact on their agonist/antagonist properties at all three LPA receptor subtypes. At LPA$_1$, the thiophosphate modification completely abolished the inhibitory effects of the original FAP analogs. At LPA$_2$ on the other hand, the thiophosphate invariably increased the efficacy of the original FAP to 100%. At the LPA$_3$ receptor, the saturated thiophosphate FAP analogs consistently showed improved inhibition of the LPA response compared to the original FAPs. Dodecyl-thiophosphate (8b) is a potent agonist and antagonist at LPA$_2$ (EC$_{50}$=1000 nM) and LPA$_3$ (K$_i$=14 nM), respectively The oleoylthiophosphate (8g) was a partial agonist at LPA$_1$ (EC$_{50}$ (E$_{max}$)=193 nM (80%)), and LPA$_3$ (EC$_{50}$ (E$_{max}$)=546 nM (78%)), and a potent and full agonist at LPA$_2$ with the EC$_{50}$ of 244 nM (E$_{max}$=175% of LPA response), lower than that of oleoyl-LPA (EC$_{50}$=300 nM).

Example 8

In Vitro Evaluation of Compound 8g for Protection of Intestinal Epithelial Cells Against Radiation or Chemotherapy Induced Apoptosis IEC-6 cells were grown in DMEM medium supplemented with 5% fetal bovine serum, insulin (10 μg/ml), gentamycin sulfate (50 μg/ml), and incubated at 37° C. in a humidified 90% air-10% $CO_2$ atmosphere. Medium was changed every other day. Sub-confluent cells were washed twice and replaced by DMEM without serum the night before experiments.

Damage and IEC-6 cell apoptosis was induced via either γ-irradiation or chemotherapy. 20 Gy single dose of [$^{137}$Cs] source γ-irradiation was used in all experiments. Serum starved IEC-6 cells were pretreated with LPA, FAP12, or compound 8g (FAP 18:1d9) for 15 minutes and then irradiated with a Mark I Model 25 Gamma Irradiator (J. L. Shepherd & Associate, San Fernando, Calif.) at a rate of 416 R/min for 4.81 minutes on a rotating platform. In some experiments, LPA was added at different times before or after irradiation. Treatment with 20 μM camptothecin of IEC-6 cells induces DNA fragmentation as measured by the ELISA assay at 16 h after treatment. DNA fragmentation was quantified using the Cell Death Detection ELISA kit from Boehringer (Indianapolis, Ind.) according to the instructions of the manufacturer. Samples were run in triplicate. A duplicate of the sample was used to quantify protein concentration using the BCA kit from Pierce (Rockford, Ill.). DNA fragmentation was expressed as absorbance units per μg protein per minute.

LPA and FAP 12 (both 10 μM) inhibited Campthotecin-induced (20 μM) DNA fragmentation in IEC-6 cells. The effect of FAPs is dose dependent as illustrated for FAP 18:1d9 thiophosphate (8g) and is comparable to that of LPA but supersedes it at concentrations above 3 μM.

Example 9

In vivo Evaluation of Compound 8g for Protection of Intestinal Epithelial Cells Against Radiation or Chemotherapy Induced Apoptosis ICR strain male mice (Harlan Laboratories, body weight 30-33 g) on a 12 h light/dark cycle and otherwise maintained on a standard laboratory chow ad libitum were starved for 16 h prior to treatment. WBI was done with a 12 Gy or 15 Gy dose using $Cs^{137}$ source at a dose rate of 1.9 Gy per minute. Groups of four mice received either 250 μl of 1 mM LPA complexed with 100 μM BSA dissolved in Hanks basal salt solution or the BSA vehicle alone 2 h prior to irradiation.

For detection of the apoptotic bodies, mice were euthanized with carbon dioxide inhalation 4 h after irradiation and the small intestine was dissected and fixed in neutral phosphate buffered isotonic 10% formalin. Four ~3- to 4-mm long segments from the small intestine were embedded in paraffin, 5 μM thick sections were cut and stained with hematoxilin and eosin. The number of surviving crypts was counted 3.5 days after irradiation.

Figure 3:
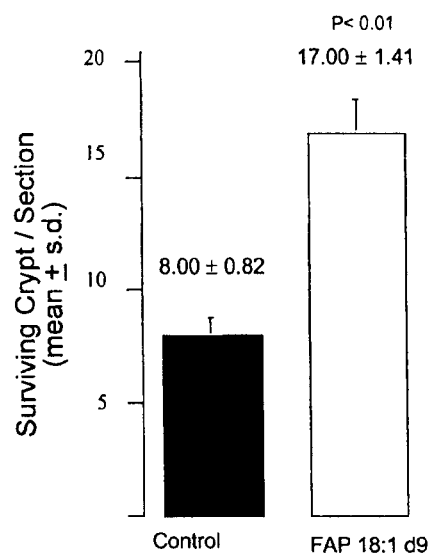
FIG. 3 is a graph illustrating that FAP 18:1d9 thiophosphate (8g) enhances crypt survival.
Figure 4:
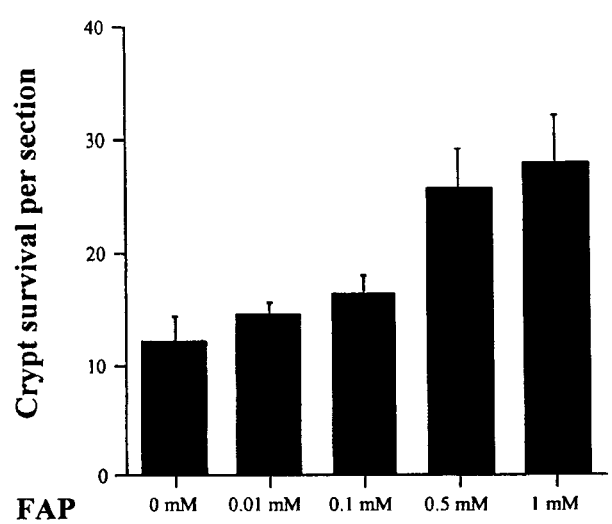
FIG. 4 is a graph illustrating the dose-dependent enhancement of crypt survival in FAP 18:1d9-treated mice.
Figure 5:
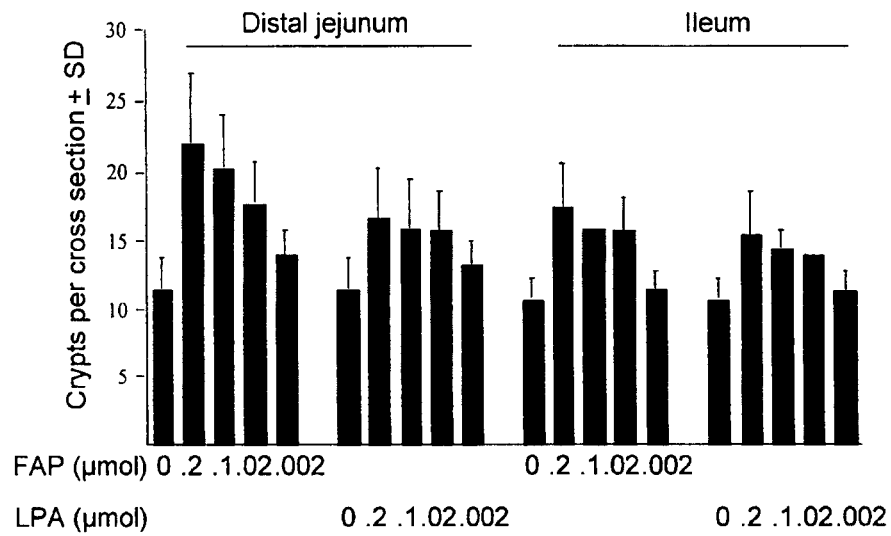
FIG. 5 is a graph demonstrating that FAP 18:1d9 elicits dose-dependent crypt survival in the ileum and jejunum of γ-irradiated mice.
Figure 6:
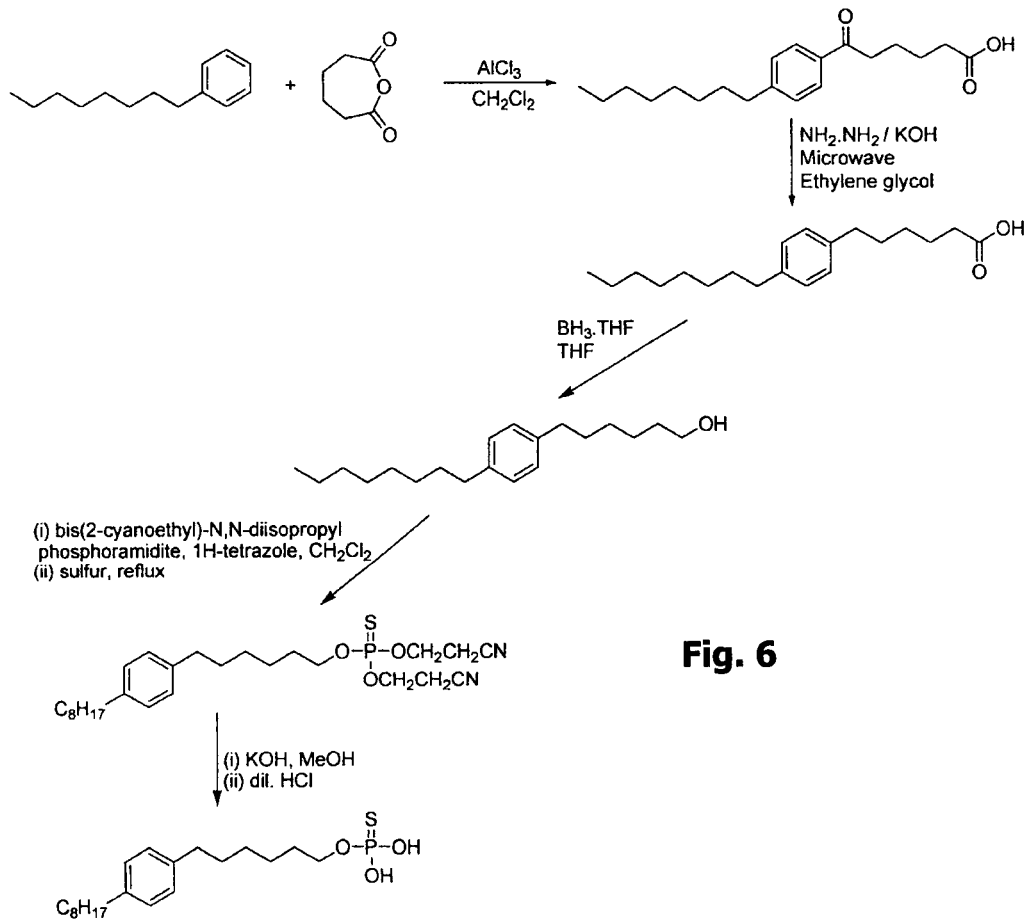
FIG. 6 illustrates a synthesis scheme for preparing thiophosphoric acid esters containing an arylalkyl $R^1$ group when $Y^1$ is also an alkyl.

FAP 18:1d9 (200 μM into the stomach 2 h prior irradiation) significantly (P>0.01) enhanced crypt survival in the irradiated animals (FIG. 3). The effect of FAP was dose-dependent (FIG. 4). The effect of FAP 18:1d9 was present in the jejunum and ileum and exceeded that of LPA (FIG. 5).

Example 10

Thiophosphates and Boranophosphates

All reagents and starting materials were purchased from Sigma-Aldrich Chemical Co., Fisher Scientific, Nu-Chek Prep Inc (Elysian, Minn.) and Toronto Research Chemicals (North York, ON, Canada) and were used without further purification. Routine thin-layer chromatography (TLC) was performed on 250 microns glassbacked UNIPLATES (Analtech, Newark, Del.). Flash chromatography was performed on 200-425 mesh silica gel (Fisher Scientific). $^1$H NMR spectra were obtained on a Bruker AX 300 (Billerica, Mass.) spectrometer. Chemical shifts for $^1$H NMR are reported as parts per million (ppm) relative to TMS. Mass spectral data was collected on a Bruker ESQUIRE electrospray/ion trap instrument in the positive and negative ion modes. Elemental analyses were performed by Atlantic Microlab Inc., Norcross, Ga.

Compounds RxBVG-I-67, RxBVG-I-77, RxBVG-I-81, RxBVG-I-82, RxBVG-I-83 were prepared following similar synthesis as used for compound 8g (see Scheme 4 below). Corresponding ammonium salts were obtained as colorless powder.

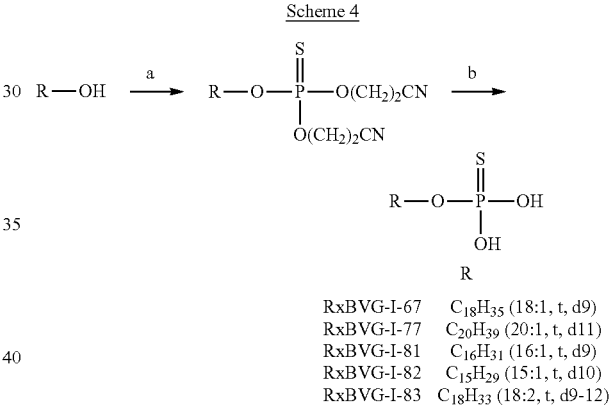

Scheme 4

| | |
|---|---|
| RxBVG-I-67 | $C_{18}H_{35}$ (18:1, t, d9) |
| RxBVG-I-77 | $C_{20}H_{39}$ (20:1, t, d11) |
| RxBVG-I-81 | $C_{16}H_{31}$ (16:1, t, d9) |
| RxBVG-I-82 | $C_{15}H_{29}$ (15:1, t, d10) |
| RxBVG-I-83 | $C_{18}H_{33}$ (18:2, t, d9-12) |

(a) (1) bis(cyanoethyl)-N,N-diisopropylphosphoramidite, 1H-tetrazole, $CH_2Cl_2$, (2) sulfur, reflux; (b) KOH, MeOH Ammonium thiophosphoryl-O-octadec-9E-enyl ester (RxBVG-I-67): Isolated as colorless powder (90% yield). $^1$H NMR (CD$_3$OD): δ 5.38 (m, 2H), 3.9 (quartet, 2H), 1.98 (m, 4H), 1.63 (m, 2H) 1.3 (br s, 22H), 0.9 (t, 3H); MS: [M−H]− at m/z 363.3.

Ammonium thiophosphoryl-O-eicos-11Z-enyl ester (RxBVG-I-77): Isolated as colorless powder (90% yield). $^1$H NMR (CD$_3$OD): δ 5.22 (m, 2H), 3.78 (quartet, 2H), 1.92 (m, 4H), 1.5 (m, 2H) 1.2 (br s, 26H), 0.8 (t, 3H); MS: [M−H]− at m/z 391.3.

Ammonium thiophosphoryl-O-hexadec-9Z-enyl ester (RxBVG-I-81): Isolated as colorless powder (90% yield). $^1$H NMR (CD$_3$OD): δ 5.24 (m, 2H), 3.7 (quartet, 2H), 1.9 (m, 4H), 1.5 (m, 2H), 1.2 (br s, 18H), 0.9 (t, 3H); MS: [M−H]− at m/z 335.3.

Ammonium thiophosphoryl-O-pentadec-10Z-enyl ester (RxBVG-1-82): Isolated as colorless powder (70% yield). $^1$H NMR (CD$_3$OD): δ 5.2 (m, 2H), 3.65 (quartet, 2H), 2.0 (m, 4H), 1.5 (m, 2H), 1.23 (br s, 16H), 0.9 (t, 3H); MS: [M−H]− at m/z 321.4.

Ammonium thiophosphoryl-O-octadeca-9Z,12Z-dienyl ester (RxBVG-I-83): Isolated as colorless powder (80% yield). $^1$H NMR (CD$_3$OD): δ 5.34 (m, 4H), 3.9 (quartet, 2H), 2.76 (m, 2H), 2.08 (m, 4H), 1.63 (m, 2H), 1.3 (br s, 16H), 0.9 (t, 3H); MS: [M−H]− at m/z 361.0.

reaction. The solvent was evaporated to give the crude product, which was dissolved in water (20 mL), and acidified with HCl. The aqueous mixture was extracted with ethyl acetate

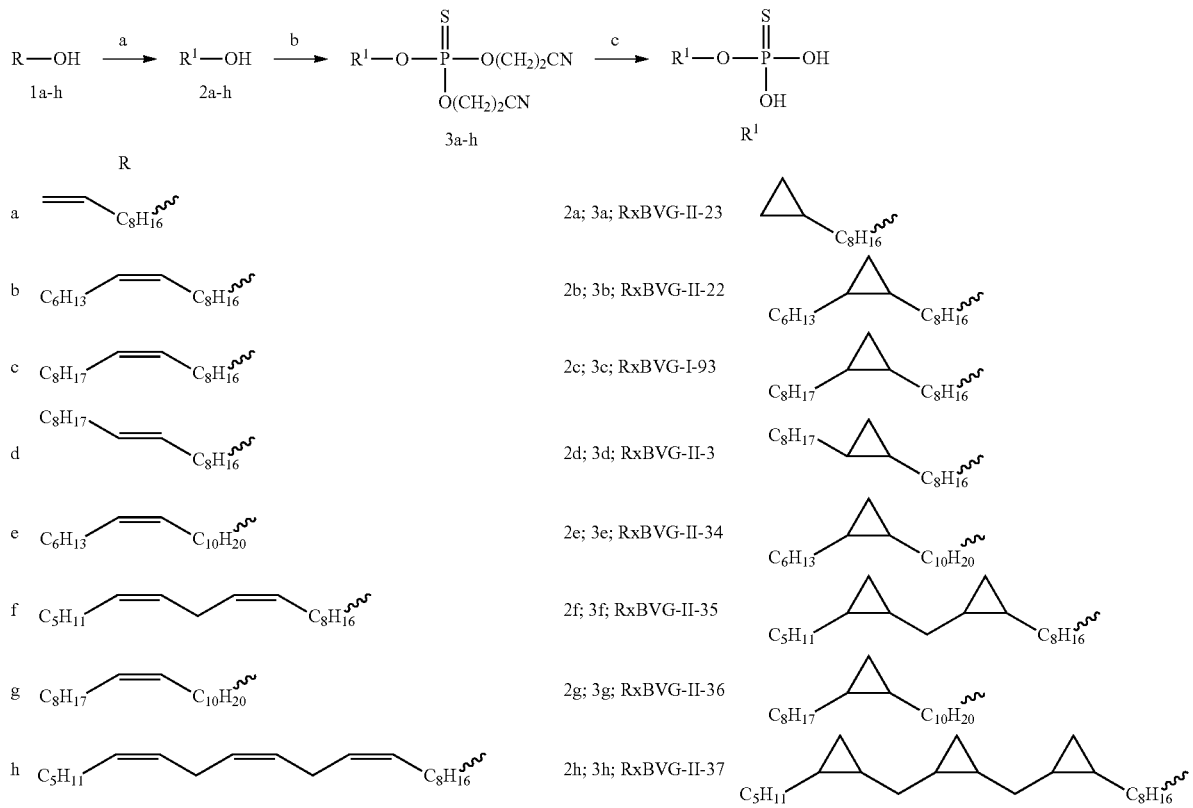

(a) 2,4,6-Trichlorophenol, Et$_2$Zn, CH$_2$I$_2$, CH$_2$Cl$_2$; (b) (1) bis(cyanoethyl)-N,N-diisopropylphosphoramidite, 1H-tetrazole, CH$_2$Cl$_2$, (2) sulfur, reflux; (c) KOH, MeOH

Synthesis of Cyclopropyl Analogs of Scheme 5

Commercially available unsaturated fatty alcohols (1a-h) were used as starting materials. Diethyl zinc (7.4 mmol) was added to a stirred solution of 2,4,6-trichlorophenol (7.4 mmol) in dichloromethane (25 mL) at −40° C. After 15 min alcohol (1.86 mmol) was added and stirring continued over night at room temperature. The reaction mixture was washed sequentially with cold aqueous 10% HCl, water, brine, dried (Na$_2$SO$_4$) and solvent was removed in vacuo. The resulting crude products were purified by silica gel chromatography using hexane/ethyl acetate (9:1) to elute the desired products 2a-h.

A solution of cyclopropyl alcohol (2.0 mmol; 2a-h), bis-(2-cyanoethyl)-N,N-diisopropyl phosphoramidite (1.085 g, 4 mmol) and 1H-tetrazole (420 mg, 6 mmol) was stirred for 30 minutes at room temperature, followed by the addition of elemental sulfur (200 mg) and the mixture was refluxed for 2 h. The reaction mixture was cooled to room temperature and solvents were evaporated under vacuum. Addition of ethyl acetate (30 mL) precipitated excess sulfur, which was filtered out, and the solvent was evaporated to give the crude mixture. The mixture was purified by flash chromatography to give the desired products (3a-h) as colorless oils.

A solution of 100 mg of 3a-3h in methanolic KOH (10 mL) was stirred for 2 h, and TLC showed the completion of the (2.times.50 mL), organic layer was dried over sodium sulfate and concentrated under vacuum to give the desired compound as light yellow colored oil. Corresponding ammonium/potassium salt was prepared by mixing thiophosphoric acid with NH$_4$OH or KOH and purified on C18 column eluting with CHCl$_3$/MeOH/NH$_3$ (5:3:1).

O-[8-(2-octyl-cis-cyclopropyl)-octyl-ol] (2c): Isolated as colorless oil (68% yield). $^1$H NMR (CDCl$_3$): δ 3.7 (t, 2H), 1.56 (m, 2H), 1.3 (br s, 26H), 0.9 (t, 3H), 0.6 (m, 2H), −0.35 (m, 2H); MS: [M+Na]− at m/z 305.2.

Thiophosphoric acid O,O'-bis(2-cyanoethyl) ester O"-[8-(2-octyl-cis-cyclopropyl)-octyl]ester (3c): Isolated as colorless oil (80% yield). $^1$H NMR (CDCl$_3$): δ 4.3 (m, 4H), 3.8 (m, 2H), 2.8 (m, 4H), 1.66 (m, 2H), 1.33 (br s, 26H), 0.93 (t, 3H), 0.6 (m, 2H), −0.37 (m, 2H); MS: [M+Na]− at m/z 524.6.

Ammonium thiophosphoryl-O-[8-(2-octyl-cis-cyclopropyl)-octyl]ester (RxBVG-I-93): Isolated as colorless powder (78% yield). $^1$H NMR (CD$_3$OD): δ 3.6 (m, 2H), 1.46 (m, 2H), 1.33 (br s, 26H), 0.9 (t, 3H), 0.6 (m, 2H), −0.31 (m, 2H); MS: [M−H]− at m/z 377.3.

Potassium thiophosphoryl-O-(8-cyclopropyl-octyl) ester (RxBVG-II-23): Isolated as colorless sticky solid (88% yield). $^1$H NMR (CD$_3$OD): δ 3.85 (m, 2H), 1.6 (m, 2H), 1.3 (br s, 10H), 1.1 (m, 2H), 0.6 (m, 1H), 0.4 (m, 1H), −0.1 (m, 2H); MS: [M−H]− at m/z 265.3.

Ammonium thiophosphoryl-O-[8-(2-hexyl-cyclopropyl)-octyl]ester (RxBVG-II-22): Isolated as colorless sticky solid (83% yield). $^1$H NMR (CD$_3$OD): δ 3.85 (m, 2H), 1.62 (m, 2H), 1.3 (br s, 22H), 0.9 (t, 3H), 0.6 (m, 2H), −0.2 (m, 2H); MS: [M−H]− at m/z 349.6.

Ammonium thiophosphoryl-O-[8-(2-octyl-trans-cyclopropyl)-octyl]ester (RxBVG-II-3): Isolated as colorless solid (90% yield). $^1$H NMR (CD$_3$OD): δ 3.7 (m, 2H), 1.65 (m, 2H), 1.35 (br s, 28H), 0.9 (t, 3H), 0.6 (m, 1H), 0.4 (m, 1H), 0.05 (m, 2H); MS: [M−H]− at m/z 377.1.

Potassium thiophosphoryl-O-[10-(2-hexyl-cyclopropyl)-decyl]ester (RxBVG-II-34): Isolated as colorless solid (79% yield). $^1$H NMR (CD$_3$OD): δ 3.71 (m, 2H), 1.45 (m, 2H), 1.25 (br s, 28H), 0.87 (t, 3H), 0.57 (m, 2H), −0.3 (m, 2H); MS: [M−H]− at m/z 377.1.

Potassium thiophosphoryl-O-{8-[2-(2-pentyl-cyclopropylmethyl)-cyclopropyl]octyl}ester (RxBVG-II-35): Isolated as colorless solid (73% yield). $^1$H NMR (CD$_3$OD): δ 3.73 (m, 2H), 1.5 (m, 2H), 1.27 (br s, 20H), 1.1 (m, 2H), 0.8 (t, 3H), 0.59 (m, 4H), −0.2 (m, 2H), 0.4 (m, 2H); MS: [M−H]− at m/z 389.3.

Potassium thiophosphoryl-O-[10-(2-octyl-cyclopropyl)-decyl]ester (RxBVG-II-36): Isolated as colorless solid (71% yield). $^1$H NMR (CD$_3$OD): δ 3.7 (m, 2H), 1.5 (m, 2H), 1.23 (br s, 30H), 0.8 (t, 3H), 0.5 (m, 2H), −0.2 (m, 2H), 0.4 (m, 2H); MS: [M−H]− at m/z 405.3.

Potassium thiophosphoryl-O-(8-{2-[2-ethyl-cyclopropylmethyl)-cyclopropylmethyl]-cyclopropylmethyl}-octyl) ester (RxBVG-II-37): Isolated as colorless solid (67% yield). $^1$H NMR (DMSO): δ 3.7 (m, 2H), 1.48 (m, 2H), 1.28 (br s, 18), 0.9 (t, 3H), 0.5 (m, 6H), −0.1 (m, 3H), −0.4 (m, 3H); S: [M−H]− at m/z 401.0

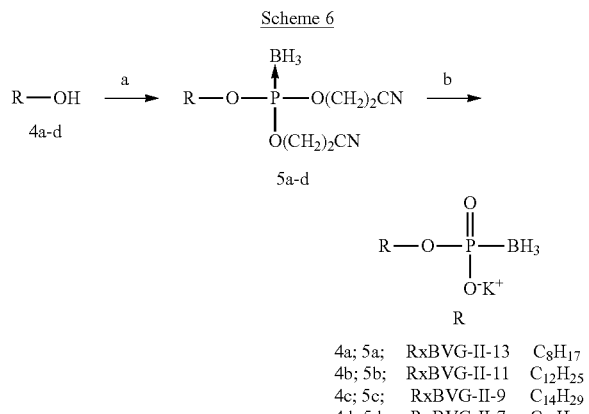

4a; 5a; RxBVG-II-13 C$_8$H$_{17}$
4b; 5b; RxBVG-II-11 C$_{12}$H$_{25}$
4c; 5c; RxBVG-II-9 C$_{14}$H$_{29}$
4d; 5d; RxBVG-II-7 C$_{18}$H$_{37}$ (a) (1) bis(cyanoethyl)-N,N-diisopropylphosphoramidite, 1H-tetrazole, CH$_2$Cl$_2$, (2) BH$_3$·DMS; (b) KOH, MeOH

Synthesis of Boranophosphate Analogs (Scheme 6)

Commercially available alcohols (4a-4-d) were used as starting materials. A solution of alcohol (0.74 mmol; 2a-h), bis-(2-cyanoethyl)-N,N-diisopropyl phosphoramidite (0.4 g, 2.3 mmol) and 1H-tetrazole (155 mg, 1.48 mmol) was stirred for 30 minutes at room temperature. The reaction mixture was cooled in an ice bath, followed by the addition of BH$_3$. DMS (2.3 mmol) and the mixture was stirred for 45 min. Solvents were evaporated under vacuum to give the crude mixture. The mixture was purified by flash chromatography to give the desired products (5a-d) as colorless oils.

A solution of 100 mg of 5a-5d in methanolic KOH (10 mL) was stirred for 2 h, and TLC showed the completion of the reaction. The solvent was evaporated to give the crude product, which was purified on C18 column using CHCl$_3$/MeOH/NH$_3$ (5:3:1).

Potassium boranophosphoryl monooctyl ester (RxBVG-II-13): Isolated as colorless powder (80% yield). $^1$H NMR (CD$_3$OD): δ 3.77 (m, 2H), 1.59 (m, 2H), 1.31 (br s, 10H), 0.89 (t, 3H), 0.75 (m, 0.5H), 0.49 (m, 1H), 0.15 (m, 1H), −0.1 (m, 0.5H); MS: [M−H]− at m/z 206.9.

Potassium boranophosphoryl monododecyl ester (RxBVG-II-11): Isolated as colorless powder (80% yield). $^1$H NMR (CD$_3$OD): δ 3.8 (m, 1H), 3.54 (m, 1H), 1.55 (m, 2H), 1.29 (br s, 18H), 0.89 (t, 3H), 0.79 (m, 0.5H), 0.5 (m, 1H), 0.2 (m, 1H), −0.1 (m, 0.5H); MS: [M−H]− at m/z 263.0. Anal. (C$_{12}$H$_{28}$BKO$_3$P.1H$_2$O)C, H.

Potassium boranophosphoryl monotetradecyl ester (RxBVG-II-9): Isolated as colorless powder (95% yield). $^1$H NMR (DMSO-d$_6$): δ 3.6 (m, 1H), 3.36 (m, 1H), 1.42 (m, 2H), 1.22 (br s, 22H), 0.83 (t, 3H); MS: [M−H]− at m/z 290.30. Anal. (C$_{14}$H$_{32}$BKO$_3$P.0.2H$_2$O)C, H.

Potassium boranophosphoryl monooctadecyl ester (RxBVG-II-7): Isolated as colorless powder (100% yield). $^1$H NMR (DMSO-d$_6$): δ 3.6 (m, 1.5H), 3.36 (m, 0.5H), 1.42 (m, 2H), 1.21 (br s, 30H), 0.83 (t, 3H); MS: [M−H]− at m/z 347.0.

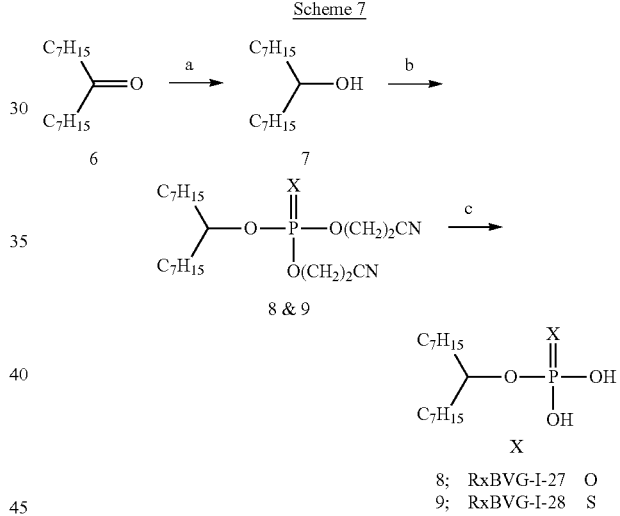

8; RxBVG-I-27 O
9; RxBVG-I-28 S (a) NaBH$_4$, MeOH; (b) (1) bis(cyanoethyl)-N,N-diisopropylphosphoramidite, 1H-tetrazole, CH$_2$Cl$_2$, (2) 30% H$_2$O$_2$, rt or sulfur, reflux; (c) KOH, MeOH

Synthesis of Branched Analogs (Scheme 7)

To a solution of ketone 6 (1 g, 4.4 mmol) in methanol (20 mL) at 0° C., NaBH$_4$ was added in small portions and stirred at ambient temperature for 2 h. Reaction mixture was poured in to ice water and extracted with chloroform (3×30 mL). Combined extracts were washed with water, brine, dried (an. Na$_2$SO$_4$) and solvent was removed in vacuo to give 7 (100%). To a stirred solution of alcohol 7 (150 mg, 0.6 mmol) and di-tert-butyl-N,N-diisopropyl phosphoramidite (320 mg, 1.2 mmol) in methylene chloride (15 mL) was added 1H-tetrazole (136 mg, 1.9 mmol). After 30 minutes of stirring the mixture was cooled to 0° C. and 0.2 mL of 30% hydrogen peroxide was added. The mixture was stirred for 1 h., diluted with methylene chloride (50 mL), washed sequentially with 10% sodium metabisulfite, saturated sodium bicarbonate, water, and brine. The organic layer was dried over anhydrous sodium sulfate, filtered, and concentrated under vacuum. The resulting crude product was purified by silica gel chromatography using hexane/ethyl acetate (7:3) to elute the desired product 8 (0.25 g, 90%).

To a solution of 120 mg of 8 in methylene chloride (15 mL), trifluoroacetic acid (1.5 mL) was added. The mixture was allowed to stir for 2 h and TLC showed the completion of the reaction. Solvents were evaporated and the residue was co-evaporated with toluene (15 mL), and purified on C18 column using $CHCl_3/MeOH/NH_3$ (5:3:1) to give RxBVG-I-27.

Ammonium phosphoryl-mono-(1-heptyl-octyl) ester (Rx-BVG-I-27): Isolated as colorless powder (100% yield). $^1H$ NMR ($CD_3OD$): δ 4.15 (m, 1H), 1.6 (m, 4H), 1.3 (br s, 20H), 0.9 (t, 6H); MS: [M−H]− at m/z 307.0.

A solution of alcohol 7 (150 mg, 0.6 mmol), bis-(2-cyanoethyl)-N,N-diisopropyl phosphoramidite (350 mg, 1.3 mmol) and 1H-tetrazole (136 mg, 1.9 mmol) was stirred for 30 minutes at room temperature, followed by the addition of elemental sulfur (62 mg) and the mixture was refluxed for 2 h. The reaction mixture was cooled to room temperature and solvents were evaporated under vacuum. Addition of ethyl acetate (15 mL) precipitated excess sulfur, which was filtered out, and the solvent was evaporated to give the crude mixture. The mixture was purified by flash chromatography to give the desired product 9 (280 mg, 96%) as colorless oil.

A solution of 250 mg of 9 in methanolic KOH (10 mL) was stirred for 2 h, and TLC showed the completion of the reaction. The solvent was evaporated to give the crude product, which was dissolved in water (20 mL), and acidified with HCl. The aqueous mixture was extracted with ethyl acetate (2×20 mL), organic layer was dried over sodium sulfate and concentrated under vacuum to give the desired compound.

Thiophosphoric acid O-(1-heptyl-octyl) ester (RXBVG-I-28): Isolated as colorless oil (93% yield). $^1H$ NMR ($CDCl_3$): δ 4.2 (m, 1H), 1.6 (m, 4H), 1.23 (br s, 20H), 0.9 (t, 6H); MS: [M−H]− at m/z 323.0.

Scheme 8

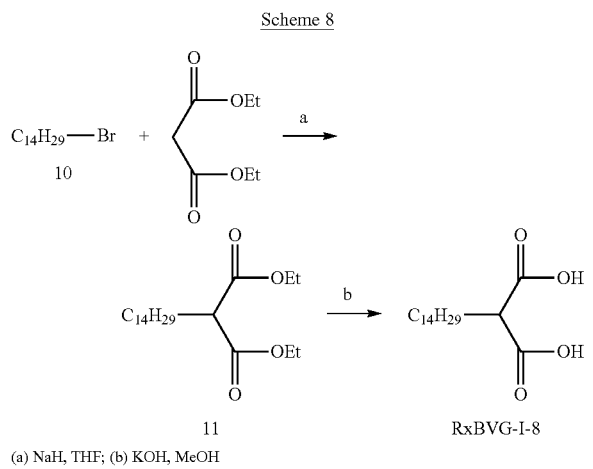

(a) NaH, THF; (b) KOH, MeOH

Synthesis of Dicarboxylic Acid Derivative (Scheme 8)

To a suspension of NaH (100 mg, 1.1 mmol) in THF (10 mL) diethylmalonate (3.8 mmol) was added and stirred for 10 min followed by addition of bromotetradecane 10 (1g, 3.6 mmol) and refluxed for 6 h. Reaction mixture was concentrated in vacuo, water (5 mL) was added and extracted with ethylacetate (3×20 mL). Combined extracts were washed with water, brine, dried (an. $Na_2SO_4$), and solvent was removed. The crude residue was purified by flash chromatography on silica gel eluting with ethylacetate/hexanes (1:24) to give 11.

A mixture of 11 (200 mg, 0.5 mmol), potassium hydroxide (100 mg, 1.5 mmol) and ethanol/water (3/1 mL) was refluxed for 3 h. Reaction mixture was cooled to room temperature and concentrated in vacuo. The residue was taken in to water, acidified with cold 10% HCl (aqs). Precipitated solid was filtered and dried to give RxBVG-I-8.

2-Tetradecyl-diethylmalonate (11): Isolated as colorless oil (68% yield). $^1H$ NMR ($CDCl_3$): δ 4.2 (m, 4H), 3.31 (t, 1H), 1.9 (m, 2H), 1.25 (br s, 30H), 0.88 (t, 3H); MS: [M+Na]− at m/z 379.3.

2-Tetradecyl-malonic acid (RxBVG-I-8): Isolated as white solid (90% yield). $^1H$ NMR (DMSO-$d_6$): δ 12.62 (br s, 2H), 3.17 (t, 1H), 1.7 (m, 2H), 1.23 (br s, 24H), 0.85 (t, 3H); MS: [M−H]− at m/z 299.0.

Scheme 9

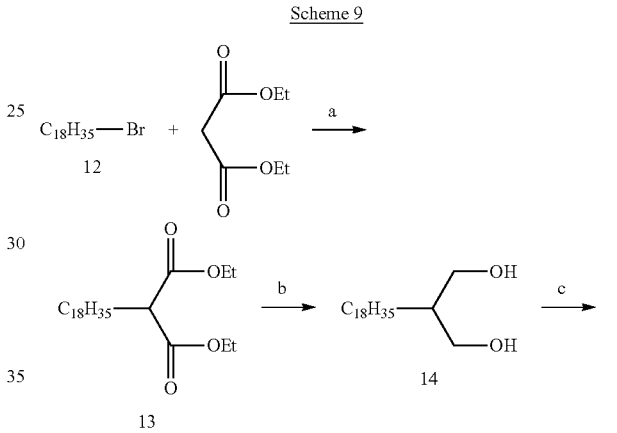

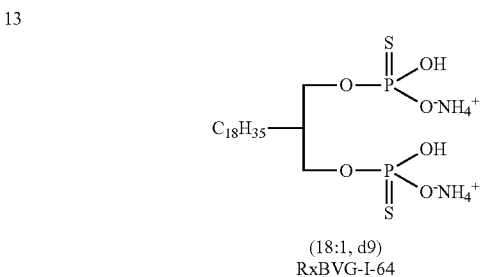

(18:1, d9)
RxBVG-I-64

(a) NaH, THF; (b) LiAlH$_4$, Et$_2$O; (c) (1) bis(cyanoethyl)-N,N-diisopropylphosphoramidite, 1H-tetrazole, CH$_2$Cl$_2$, (2) sulfur, reflux; (c) KOH, MeOH Synthesis of RxBVG-I-64 (Scheme 9)

To a suspension of NaH (170 mg, 1.1 mmol) in THF (15 mL) diethylmalonate (6.2 mmol) was added and stirred for 10 min followed by addition of oleyl bromide (1.76 g, 5.3 mmol) and refluxed for 6 h. Reaction mixture was concentrated in vacuo, water (5 mL) was added and extracted with ethylacetate (3×20 mL). Combined extracts were washed with water, brine, dried (an. $Na_2SO_4$), and solvent was removed. The crude residue was purified by flash chromatography on silica gel eluting with ethylacetate/hexanes (1:24) to give 13.

To a suspension of LiAlH$_4$ (17.1 mmol) in dry ether (20 mL) at 0° C., a solution of 13 (1 g, 2.8 mmol) in 5 mL ether was added slowly and reaction mixture was warmed to room temperature and stirred for 1 h. Moist ether was added slowly and washed with 2N HCl. The aqueous part was extracted with ethylacetate (3×15 mL). Combined extracts were washed with water, brine, dried (an.Na$_2$SO$_4$) and solvent was removed in vacuo. The crude residue was purified by silica gel column chromatography to afford 14 (90%).

A solution of diol 14 (100 mg, 0.3 mmol), bis-(2-cyanoethyl)-N,N-diisopropyl phosphoramidite (330 mg, 1.2 mmol) and 1H-tetrazole (126 mg, 1.8 mmol) was stirred for 30 minutes at room temperature, followed by the addition of elemental sulfur (38 mg) and the mixture was refluxed for 2 h. The reaction mixture was cooled to room temperature and solvents were evaporated under vacuum. Addition of ethyl acetate (15 mL) precipitated excess sulfur, which was filtered out, and the solvent was evaporated to give the crude mixture. The mixture was purified by flash chromatography to give the desired product (82%) as colorless oil. A solution of 170 mg of this oil in methanolic KOH (10 mL) was stirred for 2 h, and TLC showed the completion of the reaction. The solvent was evaporated to give the crude product, which was dissolved in water (20 mL), and acidified with HCl. The aqueous mixture was extracted with ethyl acetate (2×20 mL), organic layer was dried over sodium sulfate and concentrated under vacuum to give the desired compound which was purified on C18 column using CHCl$_3$/MeOH/NH$_3$ (5:3:1) to give RxBVG-I-64.

2-Octadec-9-enyl-diethylmalonate (13): Isolated as colorless oil (65% yield). $^1$H NMR (CDCl$_3$): δ 5.35 (m, 2H), 4.2 (m, 4H), 3.31 (t, 1H), 2.0 (m, 4H), 1.9 (m, 2H), 1.27 (br s, 30H), 0.88 (t, 3H); MS: [M+H]– at m/z 411.4.

2-Octadec-9-enyl-1,3-diol (14): Isolated as colorless oil (80% yield). $^1$H NMR (CDCl$_3$): δ 5.35 (m, 2H), 4.1 (m, 4H), 3.2 (t, 1H), 1.89 (m, 6H), 1.27 (br s, 24H), 0.88 (t, 3H); MS: [M+Na]– at m/z 349.4.

Ammonium thiophosphoryl-O-(2-thiophosphono oxymethyl-eicosyl) ester (RxBVG-I-64): Isolated as colorless sticky solid (78% yield). $^1$H NMR (DMSO-d$_6$): δ 5.3 (m, 2H), 4.23 (m, 4H), 3.37 (m, 1H), 1.9 (m, 4H), 1.7 (m, 2H), 1.23 (br s, 24H), 0.85 (t, 3H); MS: [M–H]– at m/z 517.2.

Example 11

DNA Fragmentation Assay

IEC-6 cells were obtained from the American Type Culture Collection (Manassas, Va.) and were grown in Dulbecco's modified Eagle medium (DMEM) supplemented with 10% fetal bovine serum, 10 μg/ml insulin, and 50 μg/ml gentamicin sulfate at 37° C. in a humidified 90% air/10% CO$_2$ atmosphere. The medium was changed every other day. Cells between passage 15 and 21 were used for the experiments. Newly synthesized RxBio analogs at doses ranging from 0.003 to 3 were used to pre-treat IEC-6 cells for 15 min. Apoptosis was induced by 20 μM camptothecin following the pre-treatment. DNA fragmentation was measured 6 hours after camptothecin treatment by enzyme-linked immunosorbent assay using the cell death detection ELISA$^{PLUS}$ kit from Roche (Indianapolis, Ind.) following the instruction of the manufacturer. Briefly, cells were harvested and lysed in DNA lysis buffer for 30 min. Sample lysates were collected after centrifugation at 200 rpm for 10 min. 10 μl of supernatant was loaded individually in a 96-well streptavidin-coated plate and incubated with immunoreagents (anti-histone-biotin plus anti-DNA peroxidase conjugated antibody) on a shaker for 2 h. The reaction solution was then discarded and each well was washed twice with the incubation buffer. 100 μl substrate buffer was added to each well to develop color. DNA absorbance was read at 405 nM in a microplate reader (PerkinElmer, Shelton, Conn.). Aliquots of samples were used to quantify protein concentration using the bicinchoninic acid kit (Pierce, Rockford, Ill.).

Figure 7:
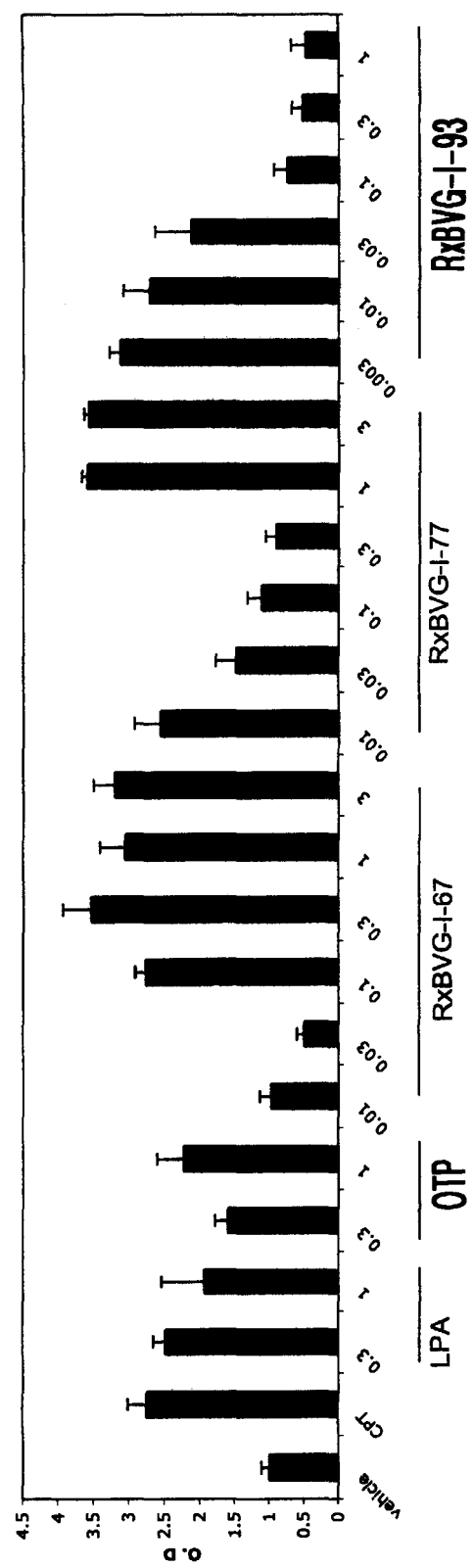
FIG. 7 is a graph illustrating the results of a DNA fragmentation assay evaluating the indicated compounds in camptothecin-induced IEC-6 cells, as described in Example 11.

As shown in FIG. 7, RxBVG-I-93 demonstrated even more efficacy than did oleoyl thiophosphate, which has proven to be a very effective radioprotectant and radiomitigator.

TABLE 4

| Compd ID | Structure | Activity |
|---|---|---|
| RxBVG-I-67 | (18:1, δ9 trans) | LPA$_3$ agonist |
| RxBVG-I-77 | (20:1, δ11 cis) | LPA$_2$ agonist |
| RxBVG-I-83 | (18:2, δ9-12 cis) | LPA$_2$ agonist |
| RxBVG-I-81 | (16:1, δ9 cis) | Pan antagonist (LPA$_{1/2/3}$) |

TABLE 4-continued
| Compd ID | Structure | Activity |
|---|---|---|
| RxBVG-I-82 | 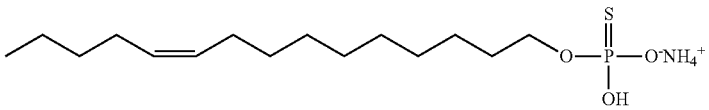 (15:1, δ10 cis) | Pan antagonist (LPA$_{1/2/3}$) |
| RxBVG-I-93 | 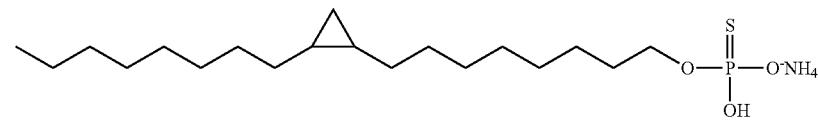 (15:1, δ9 cis) | LPA$_2$ agonist |
| RxBVG-II-3 | 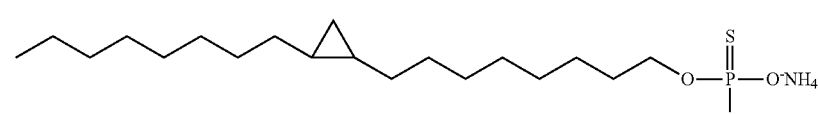 (18:1, δ9 cis) | LPA$_2$ agonist |
| RxBVG-II-22 | 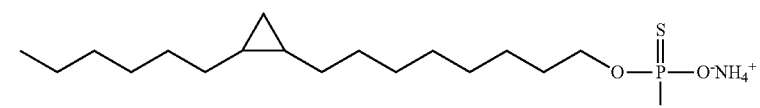 (16:1, δ9 cis) | LPA$_2$ agonist |
| RxBVG-II-23 | 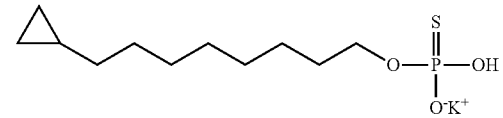 (10:1, δ9) | LPA$_2$ agonist |
| RxBVG-II-34 | 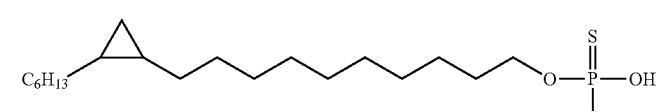 (18:1, δ11) | LPA$_2$ agonist |
| RxBVG-II-35 | 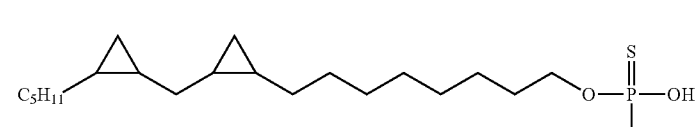 (18:1, δ9-12 cis) | LPA$_2$ agonist |
| RxBVG-II-36 | 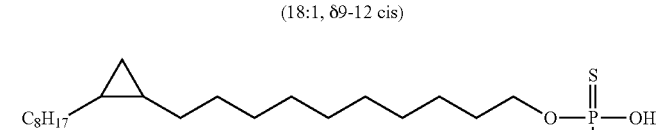 (20:1, δ11 cis) | LPA$_2$ agonist |
| RxBVG-II-37 | 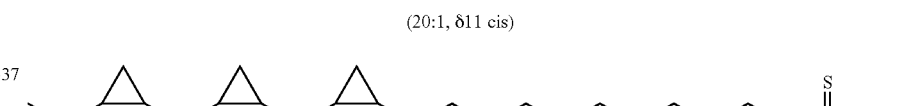 (18:3, δ9-15 cis) | LPA$_2$ agonist |

TABLE 4-continued

| Compd ID | Structure | Activity |
|---|---|---|
| RxBVG-II-7 | $C_{18}H_{37}$—O—P(=O)(O⁻K⁺)(BH₃) | LPA₂ agonist |
| RxBVG-II-9 | $C_{14}H_{29}$—O—P(=O)(O⁻K⁺)(BH₃) | LPA₂ agonist |
| RxBVG-II-11 | $C_{12}H_{25}$—O—P(=O)(O⁻K⁺)(BH₃) | LPA₂ agonist |
| RxBVG-II-13 | $C_{8}H_{17}$—O—P(=O)(O⁻K⁺)(BH₃) | LPA₂ agonist |
| RxBVG-I-8 | $C_{14}H_{29}$CH(COOH)(COOH) | LPA₂ agonist |
| RxBVG-I-27 | ($C_7H_{15}$)₂CH—O—P(=O)(O⁻NH₄⁺)(O⁻NH₄⁺) | Pan antagonist (LPA$_{1/2/3}$) |
| RxBVG-I-28 | ($C_7H_{15}$)₂CH—O—P(=S)(OH)(OH) | Pan antagonist (LPA$_{1/2/3}$) |
| RxBVG-I-64 |  (18:1, δ9cis) | LPA₃ agonist |

What is claimed is:

1. A composition comprising a compound of formula (I)

$$CQ^1\text{—}CH(X^3)\text{—}CQ^2$$
$$\quad\quad X^1\quad\quad X^2$$
(I)

wherein,
$X^1$ is $R^1\text{—}Y^1\text{-A-}$;
$X^2$ is $\text{—}Z^1\text{—}P(S)(OH)_2$;
$X^3$ is hydrogen;
A is a direct link or $(CH_2)_l$ with l being an integer from 1-30;
$Y^1$ is $(CH_2)_l$ with l being an integer from 1-30;
$Z^1$ is oxygen;
$Q^1$ and $Q^2$ are independently selected from the group consisting of $H_2$, $=NR^4$, $=O$, or a combination of H and $\text{—}NR^5R^6$;
$R^1$ is independently a straight or branched-chain $C_1$ to $C_{30}$ alkyl substituted with one or more cycloalkyl or a straight or branched-chain $C_2$ to $C_{30}$ alkenyl substituted with one or more cycloalkyl; and
$R^4$, $R^5$, and $R^6$, are independently hydrogen, a straight or branched-chain $C_1$ to $C_{30}$ alkyl, or a straight or branched-chain $C_2$ to $C_{30}$ alkenyl.

2. A composition as in claim 1 wherein the cycloalkyl is cyclopropyl.

* * * * *